United States Patent [19]

Henderson

[11] Patent Number: 5,016,469
[45] Date of Patent: May 21, 1991

[54] FLUID VISCOELASTIC TEST APPARATUS AND METHOD

[75] Inventor: Jon H. Henderson, Westminster, Colo.

[73] Assignee: Sienco, Inc., Morrison, Colo.

[21] Appl. No.: 414,682

[22] Filed: Sep. 29, 1989

[51] Int. Cl.$^5$ .................... G01N 11/10; G01N 33/49
[52] U.S. Cl. ................................................ 73/64.1
[58] Field of Search ............................. 73/64.1, 59

[56] References Cited

U.S. PATENT DOCUMENTS

| | | | |
|---|---|---|---|
| 3,741,002 | 6/1973 | Simons | 73/64.1 |
| 4,026,671 | 8/1976 | Simons et al. | 23/259 |
| 4,341,111 | 7/1982 | Husar | 73/64.1 |

FOREIGN PATENT DOCUMENTS 602825  4/1978  U.S.S.R. ................. 73/64.1

Primary Examiner—Hezron E. Williams
Assistant Examiner—Joseph W. Roskos
Attorney, Agent, or Firm—William E. Hein

[57] ABSTRACT

An instrument for testing the viscoelastic characteristics of fluids, such as blood, exhibits improved temperature regulation of the blood sample under test, includes probe drive circuitry to simplify calibration and signal conditioning, incorporates resonant frequency monitoring to detect mechanical noise disturbances, and provides automated analysis of a graphical signature, over time, of the viscoelastic characteristics of the blood sample, including a visual indication to the user of the activated clotting time period (ACT) and the rate of clot formation (RATE) of the blood sample under test, thereby improving the accuracy of the test results and simplifying operation of the instrument to permit its use by surgical personnel.

22 Claims, 16 Drawing Sheets

FLUID VISCOELASTIC TEST APPARATUS AND METHOD

REFERENCE TO RELATED PATENTS

This application is related to U.S. Pat. Nos. 3,741,002 and 4,026,671, the subject matter of which is incorporated herein by reference.

BACKGROUND AND SUMMARY OF THE INVENTION

This invention relates generally to the measurement of physical mechanical properties of fluid samples and, more specifically, to the time varying viscoelastic characteristics of a coagulating blood sample.

Measurement of the physical properties of fluids is required in many fields, such as the medical, food processing, chemical processing, and various manufacturing fields, for example. One prior art instrument for performing such fluid measurements is the Sonoclot Analyzer, manufactured by Sienco, Inc. of Morrison, Colorado. The Sonoclot Analyzer incorporates a mechanical oscillatory probe designed to oscillate at a resonant frequency of a sensor, circuit and fluid sample. This instrument generates an output signal responsive to both viscous and elastic characteristics of a fluid sample being analyzed. This output signal is plotted against time to generate a graph or signature of the changing viscoelastic characteristics of the fluid sample under test. The Sonoclot Analyzer exhibits several shortcomings. The measurement of blood coagulation characteristics, for example, is temperature sensitive. The temperature control in the prior art instrument suffers from a nominal droop error of 0.1 degree C. per degree C. change in ambient temperature. For surgical applications, typical ambient temperatures lie in the range of 12 degrees C. to 30 degrees C. The resulting sample fluid temperature error of about plus or minus 1 degree C. can corrupt the measurement and diminish confidence in the test results. In addition, manual interpretation of the graphical output signal of the prior art analyzer is both difficult for many surgical personnel and is prone to human error. Also, the analog output signal of the prior art instrument can be corrupted by mechanical noise. Simply bumping this instrument will create a noise spike on the output signal. Even noise produced by footsteps or normal conversation appear on the output signal and further complicate the required manual interpretation of the graphical output signal. Yet another shortcoming of the prior art instrument is its complicated signal conditioning circuitry and the complexity of its calibration procedure. This instrument requires high interchangeability between transducers to ensure the desired oscillation. Often performance parameters cannot be met without altering control circuit component values. Also, the oscillator within this prior art instrument incorporates a transconductance amplifier configured as a variable gain amplifier. The transconductance gain exhibits excessive temperature drift and is not referenced to a known zero gain voltage. Consequently, the transconductance gain cannot be used as an output signal. Instead, an output signal must be constructed from an AC signal within the oscillator feedback loop. This additional circuitry increases complexity and cost of the instrument.

It is therefore a principal object of the present invention to provide an instrument for testing the viscoelastic characteristics of fluids that (1) exhibits improved temperature regulation., (2) includes improved probe drive circuitry to simplify calibration and signal conditioning; (3) incorporates resonant frequency monitoring to detect mechanical noise disturbances; and (4) provides automated analysis of the graphical output signal to simplify use of the instrument by surgical personnel and to improve its accuracy.

DESCRIPTION OF THE PREFERRED EMBODIMENT

Figure 1A:
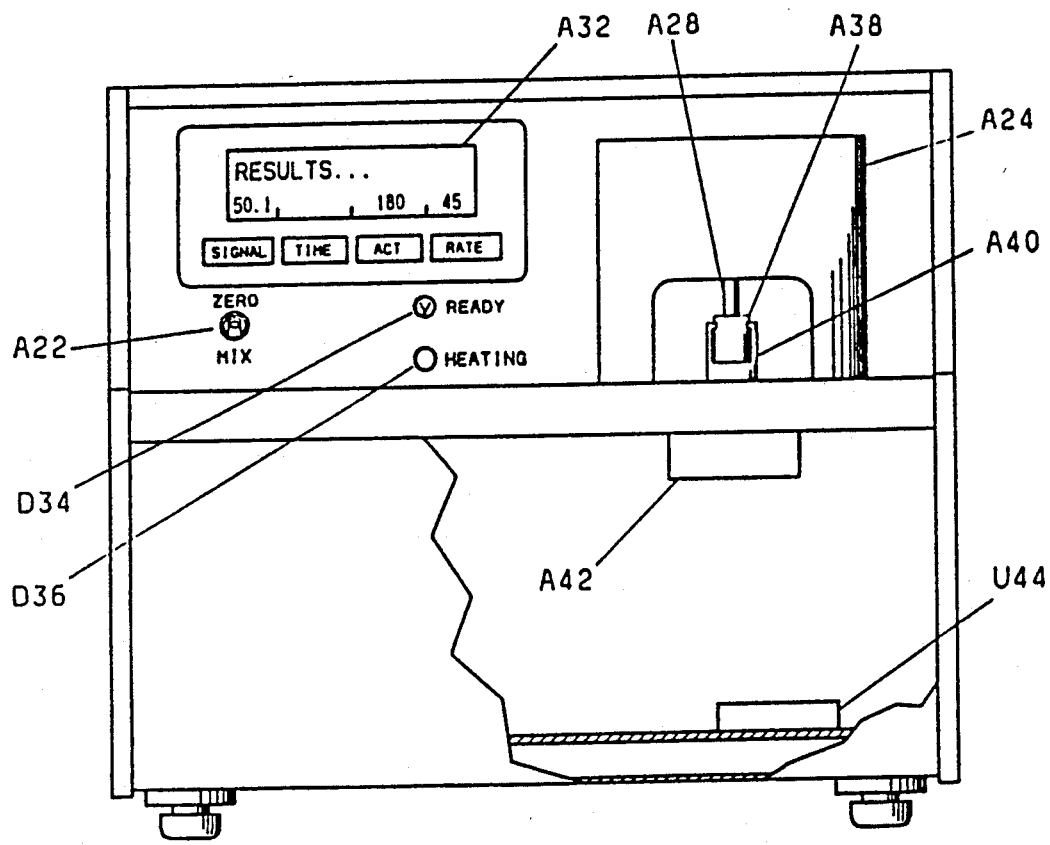
FIG. 1A is a pictorial diagram illustrating a portion of the front panel and interior of a fluid viscoelastic test instrument constructed in accordance with the present invention.
Figure 1B:
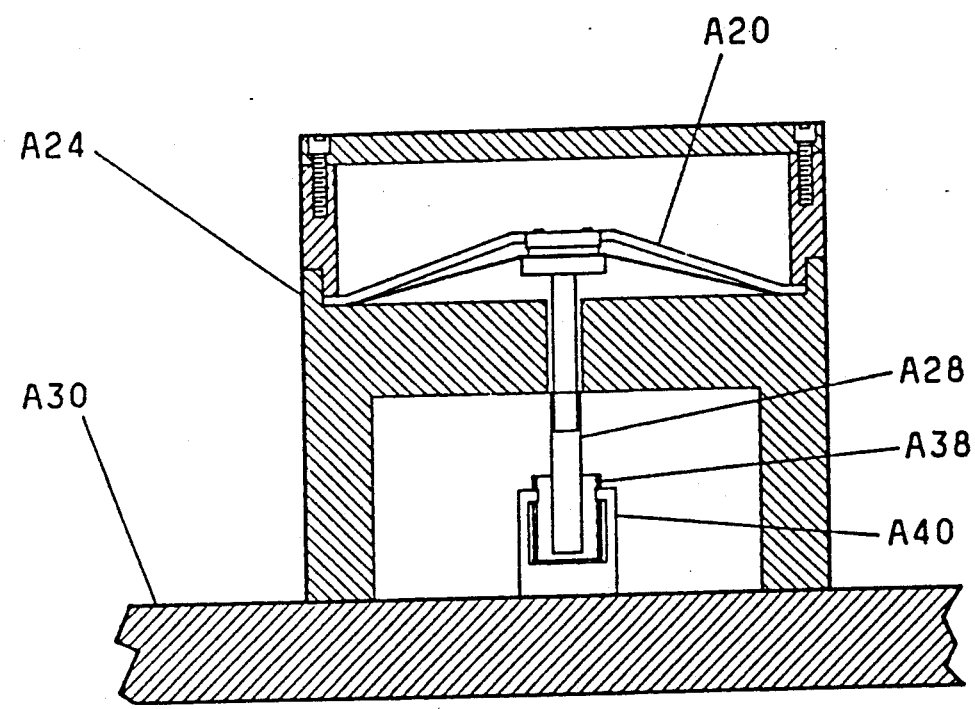
FIG. 1B is a cross-sectional diagram of a platen and a head assembly that form part of the fluid viscoelastic test instrument of the present invention.

Referring now to FIGS. 1A and 1B, there is shown a pictorial diagram of a portion of the front panel and interior of a fluid viscoelastic test instrument constructed in accordance with the present invention. A hinged head assembly A24 contains a transducer A20. Transducer A20 may simply comprise an off-the-shelf electromechanical audio speaker having an appropriate impedance. A disposable probe A28 may be removably attached to the transducer A20. A disposable cuevette A38, adapted for holding a fluid sample, is received by a cuevette holder A40. When head assembly A24 is in the lowered position, probe A28 is in contact with the fluid sample contained within cuevette A38. A ready indicator D34, which may comprise an LED, indicates that a platen A30 has heated to the desired temperature of 37 degrees C. A heating indicator D36, which may also comprise an LED, indicates that the temperature of the platen A30 is below the desired temperature. A MIX/ZERO switch A22 comprises a double pole double throw switch adapted for momentary closure in both directions. One pole generates two logic level inputs, MIX and ZERO, monitored by a microcontroller U44. The other pole uses only the MIX position of MIX/ZERO switch A22 to activate a mixing motor A42 for ten seconds when the switch is moved to the MIX position. A liquid crystal (LCD) display A32 is employed to report analysis results and operator prompts.

A particular utility for the fluid viscoelastic test instrument of the present invention lies in detecting physical characteristics of a blood sample, generating the time varying graph or signature of a blood sample during the period of time over which coagulation of the blood occurs, and analyzing that signature to extract data that quantifies variables of coagulation performance. A typical signature begins with the instrument prepared to accept a blood sample. Disposable probe A28 is attached to transducer A20. A disposable cuevette A38 having a contact activator and a mixing bar is mounted within cuevette holder A40. A blood sample is added to the cuevette A38, and MIX/ZERO switch A22 is momentarily moved to the MIX position. Mixing motor A42, magnetically coupled to the mixing bar, is operative for stirring the blood sample contained in cuevette A38 for a preferred time period of ten seconds. After stirring has stopped, head assembly 24 is manually lowered, thereby inserting probe A28 into cuevette A38. The instrument remains in this configuration during analysis of the blood sample. An analog output voltage signal V62, shown in the information flow diagram of FIG. 3 and the circuit diagram of FIG. 8B, is typically coupled to a conventional external strip chart recorder. Automated analysis of the blood sample is performed by microcontroller U44, which reports results on display A32. Following analysis of a blood sample, head assembly A24 is raised and disposable cuevette A38, containing the blood sample, and disposable probe A28 are both discarded.

Figure 2:
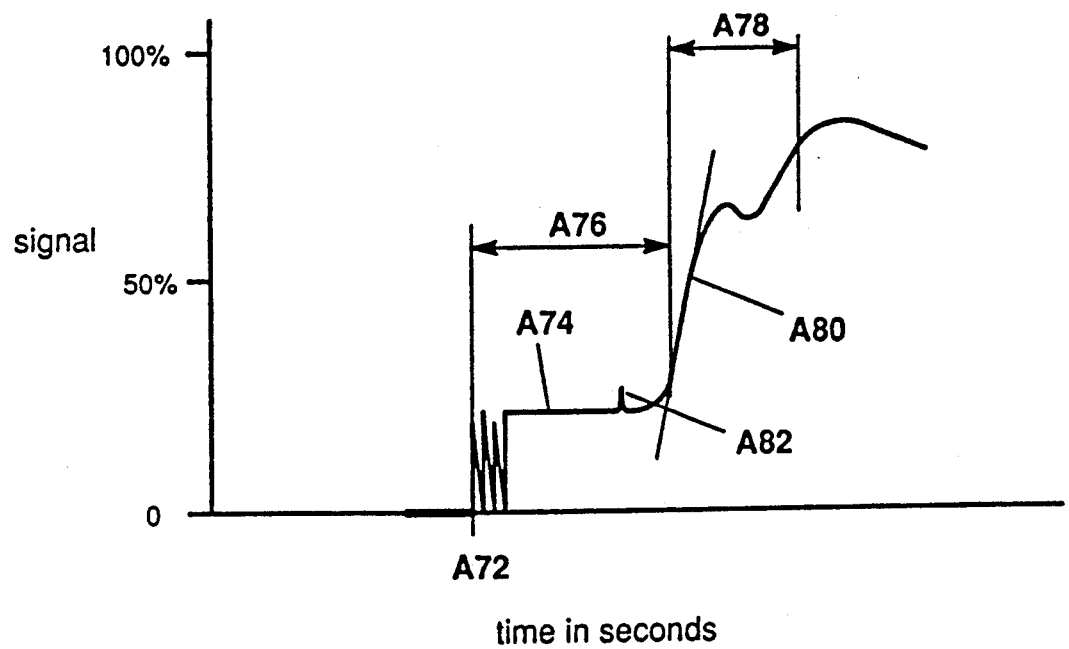
FIG. 2 is an illustration of the graphical output signal or signature produced by the fluid viscoelastic test instrument of the present invention.

Referring now to FIG. 2, there is illustrated a typical graphical output signal or signature as would be recorded on an external strip chart recorder over the period of time during which coagulation of a blood sample would occur. Vertical displacement corresponds to analog output voltage signal V62. The greater the displacement produced by this signal, the greater the value of an oscillator gain voltage signal V56. Horizontal displacement in the graph of FIG. 2 corresponds to time, typically scaled to 0.5 cm per minute.

The signature of FIG. 2 exhibits several distinct points or characteristics that relate to coagulation characteristics of the blood sample being analyzed. Time A72 shown in the signature is the point in time at which the MIX/ZERO switch A22 is moved to the MIX position. This point in time is marked on the strip chart manually. After MIX/ZERO switch A22 has been moved to the MIX position, the signature contains an indication of output noise due to mixing and lowering of probe A28 into the blood sample. Time segment A74 of the signature represents the period of time prior to the onset of coagulation of the blood sample. During this period of time the blood sample is undergoing biochemical changes necessary to allow coagulation to begin. When coagulation begins, vertical deflection of the signature commences. The activated clotting time period (ACT) A76 of the signature is defined to be the time period between actuation of the MIX/ZERO switch A22 and the point at which 1 percent deflection of full scale amplitude in the signature occurs. Time period A78 of the signature represents the period of time during which clot formation occurs. Of importance during this period of time is the rate of clot formation. Analytically, the rate of clot formation (RATE) is indicated by inflection point A80 of the signature and is defined to be the first maximum slope of the signature following the end of the activated clotting time period (ACT) A76. The instrument of the present invention automatically extracts the activated clotting time period (ACT) and the rate of clot formation (RATE) from the signature and displays these parameters to the user. The remainder of the signature represents the response of the clot to platelets and other clotting components of the blood sample. Typical mechanical noise represented by glitch A82 of the signature of FIG. 2 may be caused by bumping the instrument or by transient mechanical vibration and acts to corrupt the signal recorded by the strip chart recorder. This kind of noise is digitally filtered and ignored during the automated analysis performed the microcontroller U44.

Referring again to FIG. 1A, display A32 displays results that correspond to the graphical output illustrated in FIG. 2. The value displayed above the SIGNAL legend is a value measured by microcontroller U44 that corresponds to analog output voltage signal V62. This value is a digital representation of the vertical displacement of the signature plotted in FIG. 2. During analysis of a blood sample, the value displayed above the TIME legend is the time in seconds since MIX/ZERO switch A22 was moved to the MIX position. When an analysis is not in progress, this display position above the TIME legend is blank. When displaying results, the value displayed above the ACT and RATE legends are the activated clotting time period (ACT) A76 and the rate of clot formation (RATE) A80. During a sample analysis, the message "???" appears in display A32 above the legends ACT and RATE until the respective sample values for activated clotting time (ACT) A76 and rate of clot formation (RATE) A80 are calculated by microcontroller U44.

Figure 3:
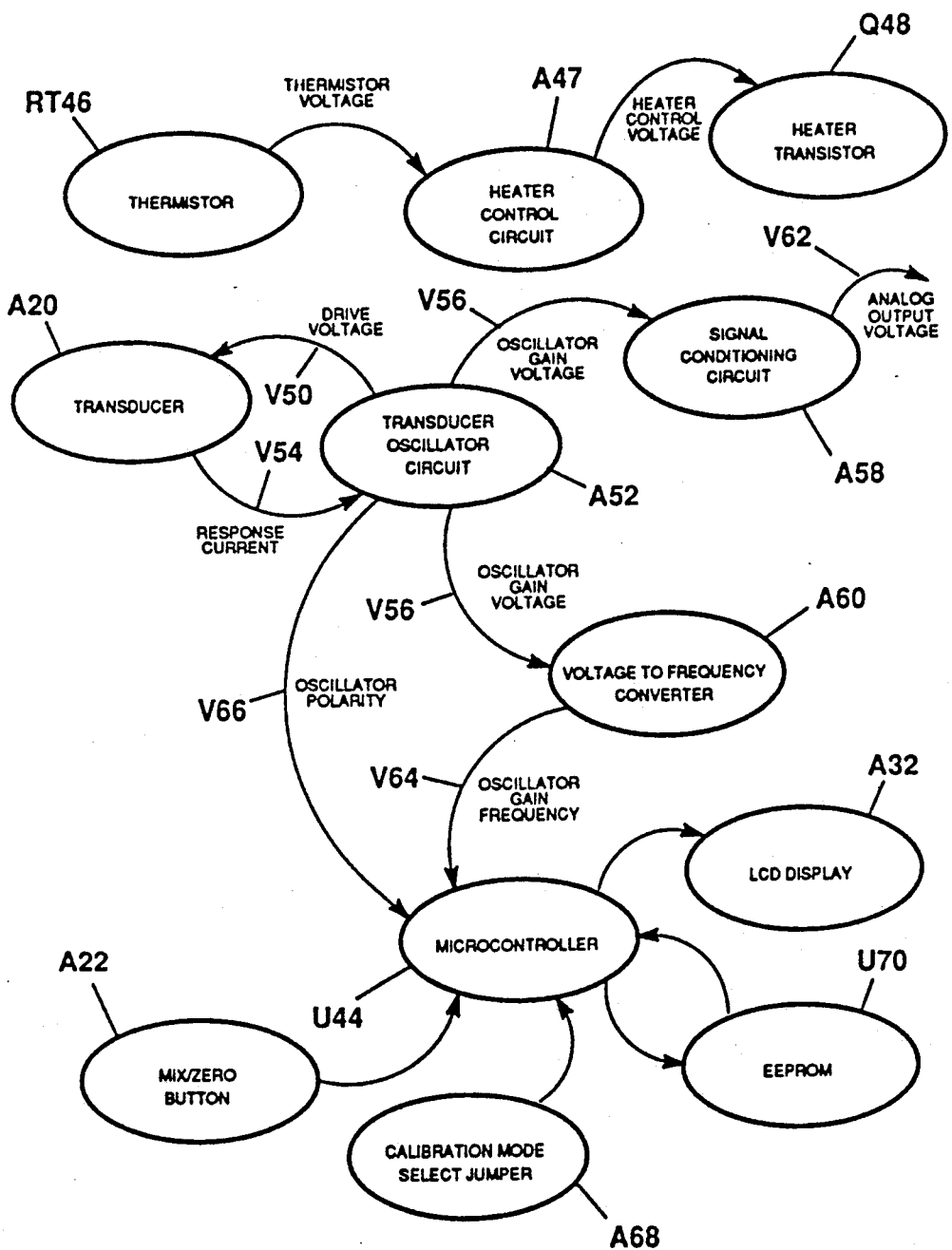
FIG. 3 is an overall information flow diagram for the fluid viscoelastic test instrument of the present invention.

Referring now to FIG. 3, there is shown an information flow diagram that highlights the overall operation of the fluid viscoelastic test instrument of the present invention. One information path describes the way in which the temperature of platen A30 is controlled. A thermistor RT46 mounted on platen A30 responds to the platen temperature. A voltage signal that varies with changing temperature is sensed within a heater control circuit A47. Heater control circuit A47 operates to vary the drive voltage to a heater transistor Q48 to maintain platen A30 at a desired temperature. Another information path illustrated in the flow diagram of FIG. 3 describes the way in which a fluid sample is viscoelastically measured and analyzed by the instrument. Transducer A20 is mechanically excited by a transducer drive voltage signal V50 generated by a transducer oscillator circuit A52. The mechanical displacement of transducer A20 is related to transducer response voltage signal V54. Transducer oscillator circuit A52 also generates oscillator gain voltage signal V56. This voltage signal varies with different fluid characteristics. Oscillator gain signal V56 connects to both a signal conditioning circuit A58 and a voltage-to-frequency converter A60. Signal conditioning circuit A58 generates analog output voltage signal V62 suitable for driving an external strip chart recorder. Voltage-to-frequency converter A60 generates oscillator gain frequency signal V64, a frequency representation of oscillator gain voltage signal V56. Oscillator gain frequency signal V64 is coupled to microcontroller U44. Transducer oscillator circuit A52 also generates an oscillator polarity signal V66, a logic signal indicative of the polarity of the transducer drive voltage signal V50. Oscillator polarity signal V66 is monitored by microcontroller U44. Microcontroller U44 also receives logic or data inputs from MIX/ZERO switch A22, calibration mode select jumper A68, and EEPROM U70. Microcontroller U44 generates the control logic required to drive liquid crystal display (LCD) A32 and to store date in EEPROM U70.

Figure 4A:
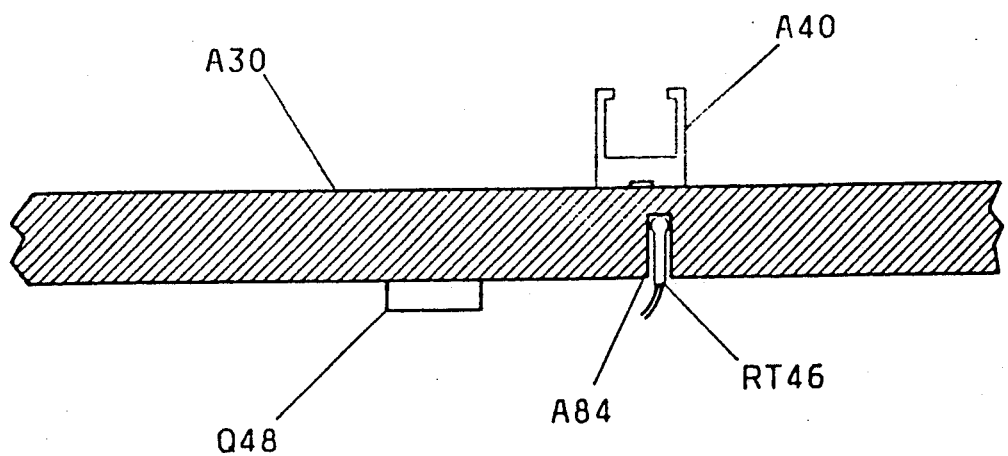
FIG. 4A is a front cross-sectional view of the platen of FIG. 1B.
Figure 4B:
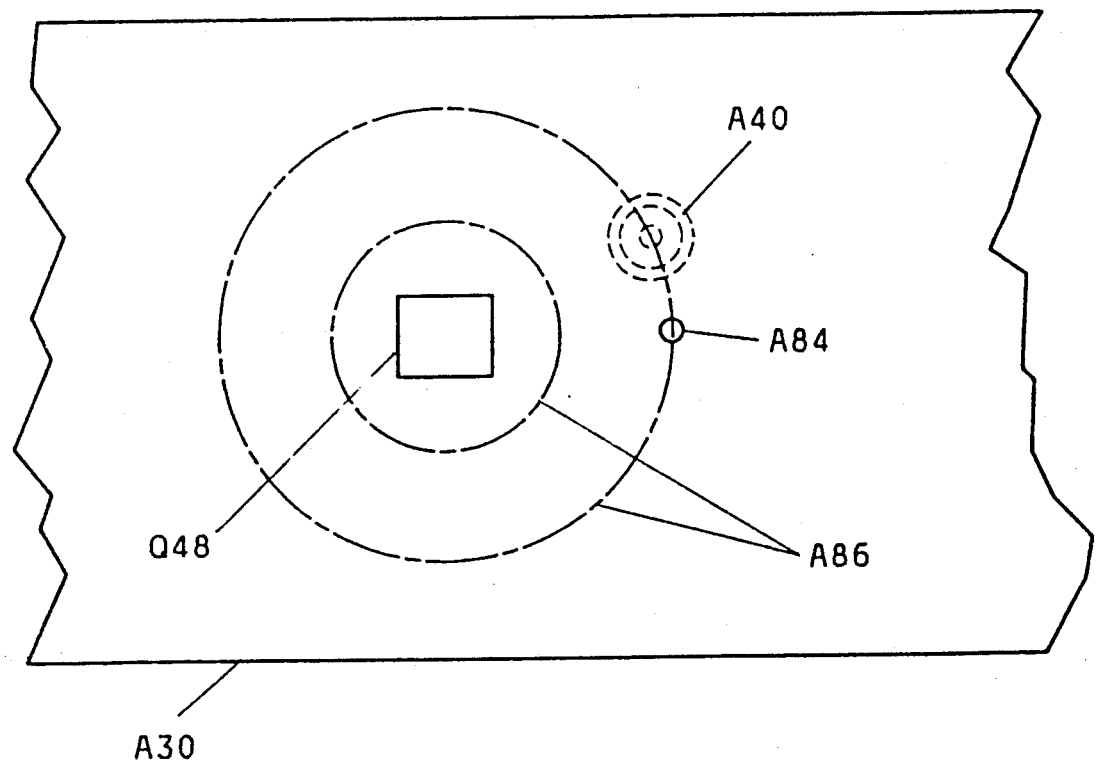
FIG. 4B is a bottom view of the heating control components located on the platen of FIGS. 1B and 4A.

As stated above, the temperature of platen A30 is controlled by heater control circuit A47. FIG. 4A is a front cross-section view of platen A30 and also illustrated a temperature sensor well A84, cuevette holder A40, and transistor Q48 and thermistor RT46 that form a portion of heater control circuit A47. FIG. 4B illustrates the same components in a bottom view. The dashed lines A86 of FIG. 4B identify assumed constant temperature lines that develop around heater transistor Q48 and extend across platen A30. The purpose of heater control circuit A47 is to maintain the temperature of the fluid sample within disposable cuevette A38 to the desired temperature of 37 degrees C. Heater control circuit A47 drives heater transistor Q48 to regulate the temperature of thermistor RT46 mounted in temperature sensor well A84. The location of temperature sensor well A84 has been selected to lie along an assumed constant temperature line extending through cuevette holder A40. Consequently, the temperature at cuevette holder A40 is regulated to approximately the same temperature as that of temperature sensor well A84.

Figure 5:
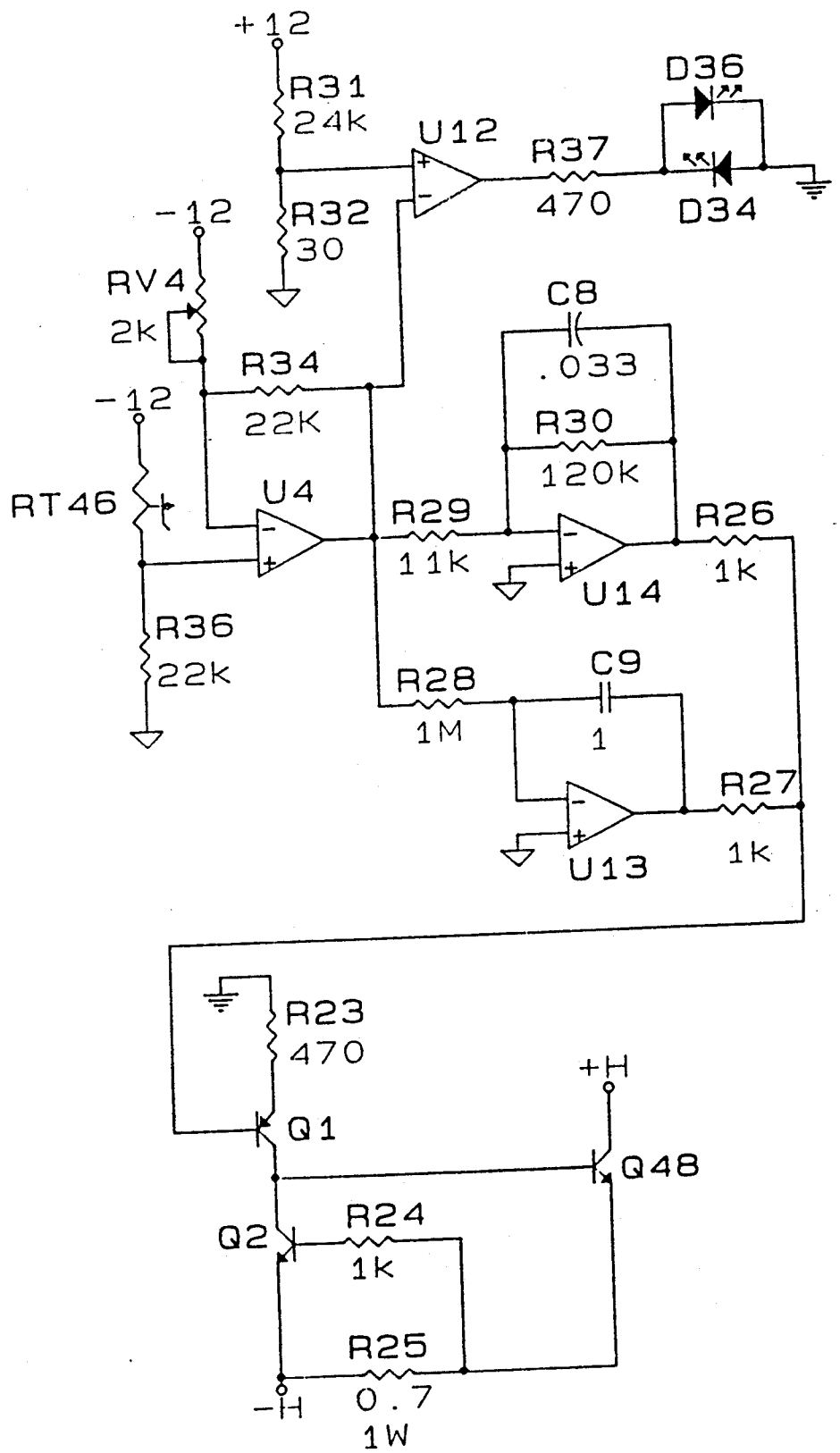
FIG. 5 is a detailed schematic diagram of a heater control circuit employed in the fluid viscoelastic test instrument of the present invention.

Referring now to FIG. 5, there is shown a detailed schematic diagram of the heater control circuit A47. Heater control circuit A47 is a proportional plus integral feedback control circuit that regulates the temperature of thermistor RT46 to a desired control temperature. The integral feedback component corrects the droop error inherent in the heating circuit of the prior art instrument. The desired control temperature is adjusted by means of variable resistor RV4. Thermistor RT46 is connected within a resistor bridge amplifier consisting of gain resistors R34 and R36, operational amplifier U4, and variable resistor RV4. The output of operational amplifier U4 is a voltage that varies with the changing resistance of thermistor RT46. Neglecting offset voltages, when the temperature sensed by thermistor RT46 is above or below the desired control temperature, the voltage generated by operational amplifier is positive or negative, respectively. The output of operational amplifier U4 is coupled to comparator U12 that drives either heating indicator D36 or ready indicator D34, proportional amplifier U14, and integrating amplifier U13. The outputs of proportional amplifier U14 and integrating amplifier U13 generate the control current for heater transistor Q48. The proportional gain is increased or decreased by either decreasing or increasing the values of resistors R26 and R29 or by increasing or decreasing the value of resistor R30. The integral gain is increased or decreased by decreasing or increasing the value of resistors R28 or R27 or capacitor C9. Resistor R25 provides current limiting for the heater transistor Q48. The voltages H+ and H− are the positive and negative outputs from a full bridge rectifier. Ground potential is referenced to a voltage at a nominal midpoint between H+ and H−. The components shown provide suitable performance of (1) rapid adjustment to an ambient temperature change, (2) control stability, and (3) tight temperature regulation.

Figure 6:
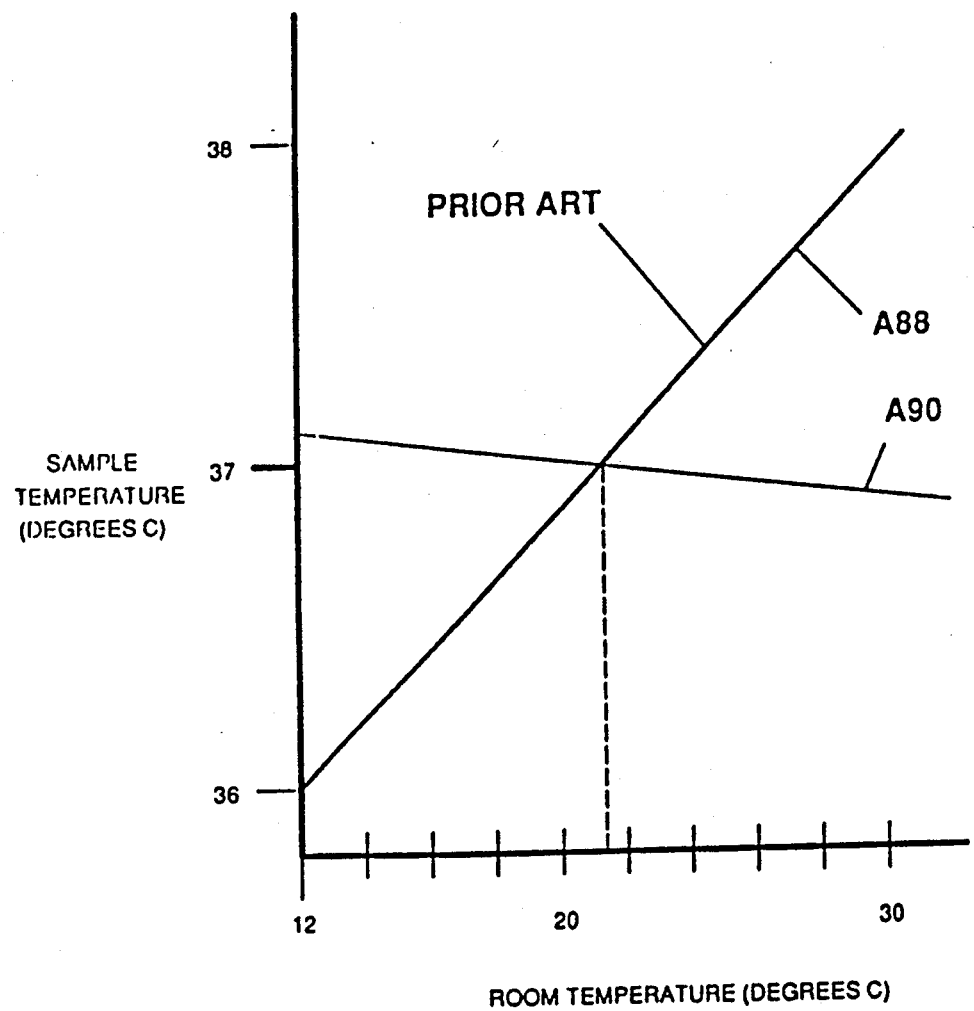
FIG. 6 is a graph illustrating the temperature regulation improvement provided by the heater control circuit of FIG. 5 over that of the prior art.

Referring now to FIG. 6 there is shown a temperature regulation curve A90 associated with heater control circuit A47 and a second temperature regulation curve associated with the instrument of the prior art. The reasons for the significantly improved temperature regulation exhibited by heater control circuit A47 are that it incorporates integral feedback in its control loop and that temperature well A84 for thermistor RT46 is positioned on an approximate constant temperature line with cuevette holder A40.

Figure 7:
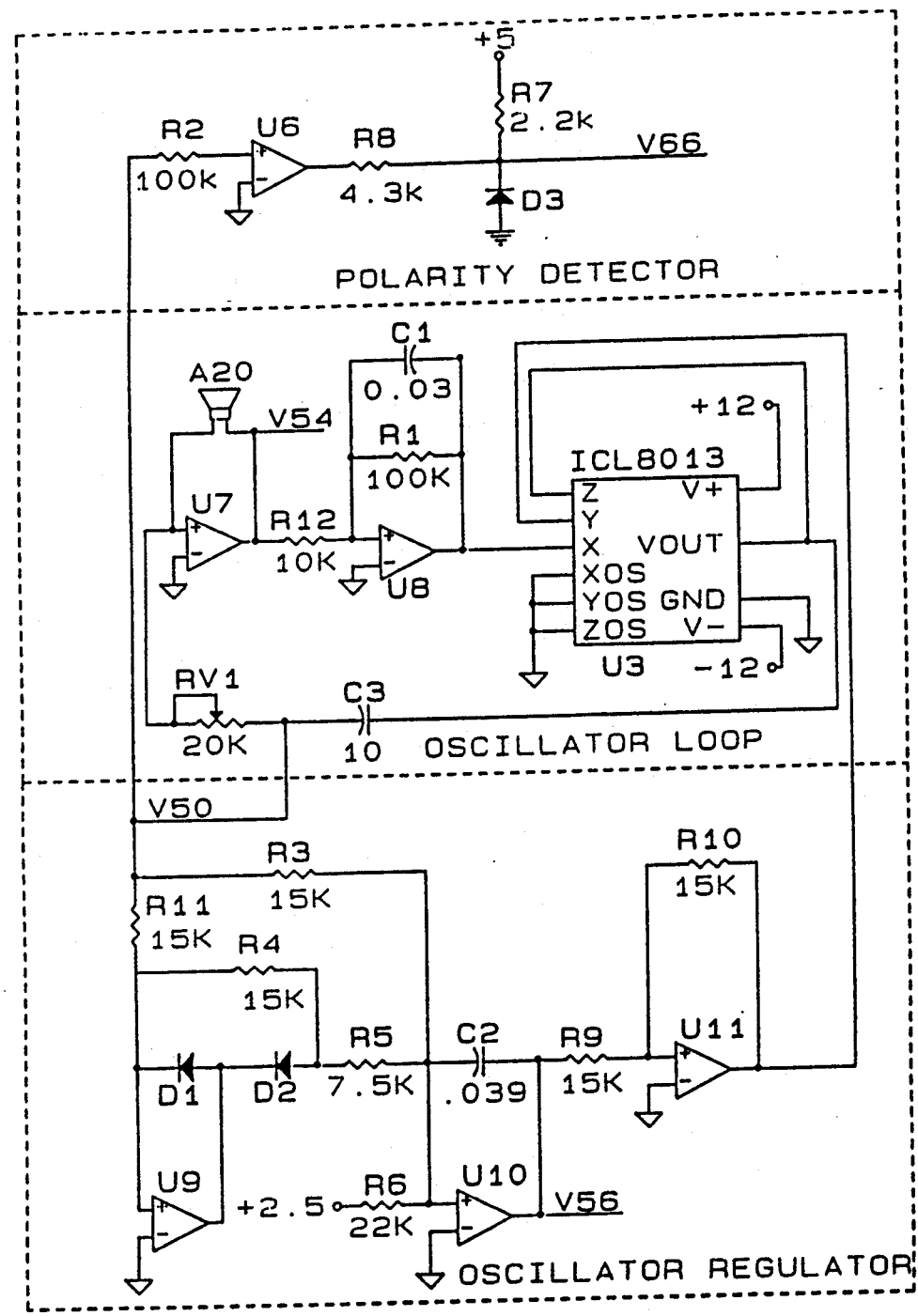
FIG. 7 is a detailed schematic diagram of a transducer oscillator circuit employed in the fluid viscoelastic test instrument of the present invention.

Referring now to FIG. 7, there is shown a detailed schematic diagram of transducer oscillator circuit A52. Transducer oscillator circuit A52 comprises an oscillator loop and an interconnecting oscillator gain regulator loop. The oscillator loop consists of a transducer drive operational amplifier U7, and inverting gain and filter amplifier U8, a multiplier U3, a capacitor C3, and a variable resistor RV1. Capacitor C1 filters any high frequency signals or noise from transducer drive operational amplifier U7. This avoids possible undesirable high frequency oscillation. Capacitor C3 blocks any DC offset voltage around the entire oscillator loop. Variable resistor RV1 is used to calibrate the oscillator loop to desired performance.

For oscillation to occur, the gain of the oscillator loop is regulated to unity at the natural frequency of the fluid sample, transducer, and oscillator loop system. For all other frequencies the loop gain is less than unity, and oscillation does not occur. Consequently, the waveforms of both a transducer drive voltage signal V50 and a transducer response voltage signal V54 exhibit a sinusoidal shape at the natural frequency of the oscillator loop system. This loop gain is the product of all gains around the oscillator loop. During operation all gains around the oscillator loop are fixed except the gain of transducer drive operational amplifier U7 and multiplier U3. The gain of transducer operational amplifier U7 varies with changing fluid sample properties. The gain of multiplier U3 is regulated to vary inversely with changes in the gain of transducer operational amplifier U7.

The oscillator gain regulator loop varies the gain of multiplier U3 by varying oscillator gain voltage V56 that connects to the Y input of multiplier U3 through inverting amplifier U11. Input to the gain adjustment loop is transducer drive voltage signal V50. This input voltage signal is applied to a precision AC to DC filter/integrator comprising operational amplifiers U9 and U10, resistors R3, R4, R5, R6, and R11, diodes D1 and D2, and capacitor C2. Capacitor C2 integrates the difference between two signals that represent a rectified version of transducer drive voltage signal V50 and a setpoint current driven from a 2.5 V reference voltage through resistor R6. When the magnitude of the transducer response is less than or greater than the setpoint current, the voltage across capacitor C2 increases or decreases. This voltage is oscillator gain voltage signal V56.

The preferred circuit of FIG. 7 serves to regulate transducer drive voltage signal V50. Alternatively, this circuit can be readily modified to regulate transducer response voltage signal V54. Actually, any combination of drive voltage and response voltage could be used as input to the gain adjustment loop. Ensuring both oscillation self starting and stability may not be possible for all input combinations. The chosen approach is adequate, simple, self starting, and stable.

The circuit of FIG. 7 also contains a polarity detector circuit to generate oscillator polarity signal V66 from transducer drive voltage signal V50. The input to the polarity detector circuit could be taken from many points around the transducer oscillator loop. The chosen input, transducer drive voltage signal V50, is adequate. Using transducer voltage signal V50 has the advantage of being regulated to a constant magnitude, which helps ensure proper operation of the polarity detector circuit across a wide range of fluid samples.

Figure 8:
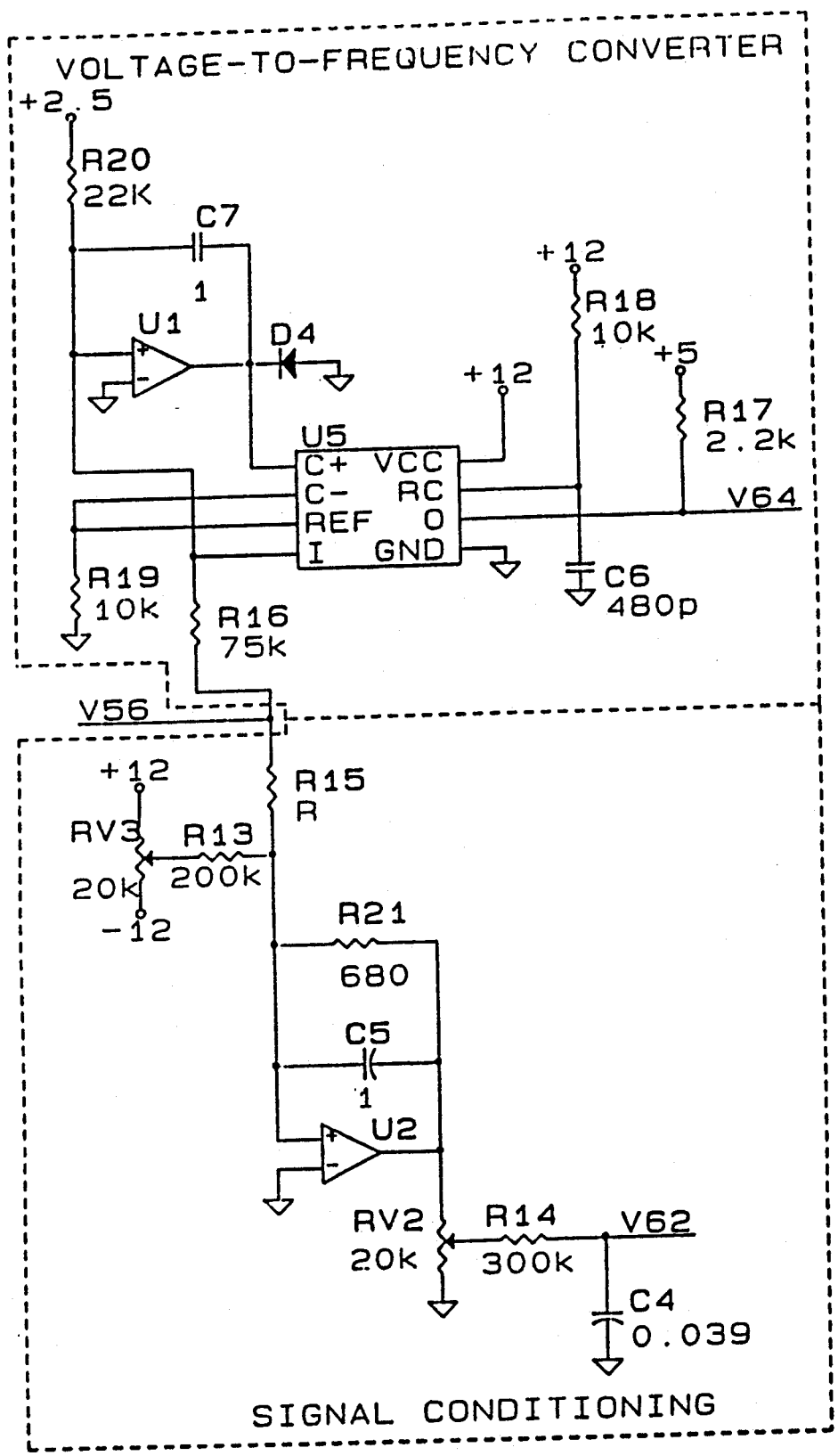
FIG. 8 is a detailed schematic diagram of a voltage-to-frequency converter and a signal conditioning circuit employed in the fluid viscoelastic test instrument of the present invention.

Referring now to FIG. 8, there is shown a preferred circuit implementing the signal conditioning circuit A58 of FIG. 3. This circuit converts oscillator gain voltage signal V56 to a 0 to 10 mV signal suitable for input to a strip chart recorder. Variable resistors RV3 and RV2 serve to adjust the offset and gain, respectively, of analog output voltage signal V62. Calibration of signal conditioning circuit A58 is described hereinbelow.

Microcontroller U44 is operative for calculating values of the oscillator gain voltage signal V56 that are software calibrated to be equivalent to analog output voltage signal V62. From multiple, time sequenced measurements of oscillator gain voltage signal V56, microcontroller U44 calculates the activated clotting time period (ACT) A76 of the signature of FIG. 2 and the rate of clot formation (RATE) A80 for a blood sample under test.

Microcontroller U44 comprises an Intel 80C196 processor. This processor was selected for its ability to conveniently and rapidly measure the frequency of digital signals and the availability of a high level C programming language compiler. Microcontroller U44 operates at 8 megahertz. The only RAM used within the instrument is the RAM internal to microcontroller U44. LCD A32, a program EPROM, EEPROM U70, a microcontroller monitor chip, digital frequency sources, and calibration mode select jumper A68 are all coupled to microcontroller U44. Display A32 comprises an LCD that is 2 rows of 16 characters in length. An Intel 87C257 EPROM provides 32K by 8 bits of program storage. EEPROM U70 comprises a Xicor X2402 that provides 256 by 8 bytes of electrically alterable read only memory. This memory is used to store calibration settings described hereinbelow. EEPROM U70 is a serial device compatible with the Phillips/Signetics Inter-Integrated Circuit (IIC) communications protocol. The required clock and data lines are controlled by software routines within microcontroller U44. This software implements the timing requirements defined in the IIC specifications available from Phillips or Signetics. These software routines can be readily derived from the IIC communications protocol specifications.

The digital frequency sources coupled to microcontroller U44 comprise oscillator polarity signal V66 and oscillator gain frequency signal V64. These frequency inputs are used to analyze and filter oscillator gain voltage signal V56. Calibration mode select jumper A68 represents a digital input to microcontroller U44. With a jumper installed, a logical 0 is monitored by the microcontroller U44. Without a jumper, microcontroller U44 monitors a logical 1. Calibration mode select jumper A68 is employed as part of the calibration process described hereinbelow.

Oscillator gain voltage signal V56 is an analog signal and must be converted to a digital representation for utilization within microcontroller U44. The necessary analog to digital conversion requires high accuracy for rapid and accurate calculation of the rate of clot formation (RATE) A80 for a blood sample under test. Considering the total conversion accuracy accounting for all error components and a delta time of 10 seconds for the calculation of rate of clot formation (RATE), a conversion accuracy of plus or minus 0.01 percent on measurements of oscillator gain voltage signal V56 yields an accuracy for rate of clot formation (RATE) of plus or minus 0.12 percent per minute.

Three major error components must be minimized to achieve accurate digital measurement of oscillator gain voltage signal V56. These are extraneous mechanical noise, AC ripple on oscillator gain voltage signal V56, and analog to digital conversion error. Extraneous mechanical noise corrupts oscillator gain voltage signal V56. This noise results from a variety of unavoidable sources including walking, talking, or simply touching the instrument. For convenient automated analysis of a blood sample signature, noise corrupted values of oscillator gain voltage signal V56 are identified within the microcontroller program, and the bad data is discarded. This approach has the tremendous advantage of allowing the analysis software to assume each measurement of oscillator gain voltage signal V56 is accurate. Extensive digital filtering is thereby avoided, and high accuracy is achieved.

Noise is identified within microcontroller U44 by monitoring oscillator polarity signal V66, calculating the period of this signal, and comparing this period with the Previous period measurement. When significant variance (greater than plus or minus 64 microseconds) between consecutive periods of oscillator polarity signal V66 is observed, the noise filter activates. The 64-microsecond period variance has been selected rather arbitrarily to detect many noise sources, including nearby talking. This tolerance may be too tight for locations with higher ambient noise levels than the laboratory locations typically encountered.

Whenever the noise filter detects noise, the filter remains active for two seconds. This time delay allows oscillator gain voltage signal V56 to stabilize from a noise event before measurement.

The AC ripple and analog to digital conversion errors are minimized by performing an integrating analog to digital conversion. The conversion is performed by both electronic hardware and software with microcontroller U44.

A portion of the electronic circuitry of FIG. 8 transforms oscillator gain voltage signal V56 to oscillator gain frequency signal V64. This preferred voltage to frequency circuit is derived from the precision voltage to frequency converter described in *Linear Databook* 2, 1988 *Edition*, National Semiconductor Corporation, Pages 3-290. The components have been selected to have a frequency offset of nominally 1000-2000 hertz for a very low viscosity sample such as air and a nominal frequency range of 6000-9000 hertz between a 400 centipoise fluid sample and air.

Minimization of AC ripple is an inherent feature of an integrating analog to digital conversion method. AC ripple error is further minimized by adjusting the integration period to an integral number of the AC ripple cycles. The vast majority of AC ripple is at the frequency of the oscillator loop. This frequency is the frequency of oscillator polarity signal V66. The conversion software synchronizes the start and end times of integration of oscillator gain frequency signal V64 with oscillator polarity signal V66. Consequently, the measured frequency of oscillator gain frequency signal V64 is an average value uncorrupted by AC ripple at the oscillator frequency.

The resolution of the analog to digital conversion is the resolution of the measurement of oscillator gain frequency signal V64. Microcontroller U44 has the ability to measure time events with a resolution of 2 microseconds. The integration of oscillator gain frequency signal V64 is performed for at least 0.5 seconds. Consequently, the theoretical resolution in measuring oscillator gain frequency signal V64 is better than 0.1 hertz for frequencies less than 10,000 hertz. All frequency measurements are in units of 0.2 hertz. New measurements are made at approximately one second intervals. Whenever noise has been detected within the previous two seconds, no measurements are performed.

Measurements of oscillator gain frequency signal V64 are scaled by calibration coefficients to be equivalent to analog output voltage signal V62. Additionally, the time rate of change of measurements of oscillator gain frequency signal V64 are scaled by the same calibration coefficients to calculate the slope of analog output voltage signal V62. To calculate this slope a time-stamped history of the most recent measurements of oscillator gain frequency signal V64 are stored in the memory of microcontroller U44. After each measurement of oscillator gain frequency signal V64, microcontroller U44 updates variables that correspond to analog output voltage signal V62 and its current slope.

The software instructions executed by microcontroller U44 comprise several routines continually performed whenever the fluid viscoelastic test instrument is powered. These routines or tasks are organized into normal tasks performed in rotating priority and interrupt tasks to handle time critical activities. Normal tasks are each performed at least every 0.05 seconds. Software routines related to measurement of the oscillator gain voltage signal and the associated digital filtering are described in the flowcharts of FIGS. 10A–E and a listing of the C language implementation of these software routines follows this detailed description.

Calibration of the instrument involves five separate calibration tasks. These involve calibration of the temperature setpoint of platen A30, adjustment of the transducer oscillator circuit A52 to desired oscillation, calibration of the offset and gain of signal conditioning circuit A58, and calibration of the offset reference and gain reference of microcontroller U44.

As described above, the temperature setpoint of platen A30 is adjusted by means of variable resistor RV4. A thermometer is placed at the cuevette holder A40. Variable resistor RV4 is then adjusted until the desired temperature (37 degrees C.) is read on the thermometer. After adjusting variable resistor RV4, approximately five minutes must be allowed for the platen A30 to reach a new equilibrium temperature.

Transducer oscillator circuit A52 is adjusted using variable resistor RV1 to achieve oscillation across a range of viscosities from near zero (for air) to 400 centipoise. At 400 centipoise, oscillator circuit A52 should be near but below saturation. Cannon Instrument Company offers reference viscosity fluids.

After oscillator circuit A52 has been adjusted, offset and gain for both signal conditioning circuit A58 and microcontroller U44 are calibrated. Offset calibration is performed first, followed by gain calibration. In order to accomplish offset calibration, a probe A28 is placed on transducer A20 and head assembly A24 is closed. This configuration is referred to as probe-in-air. To perform gain calibration, the procedure is identical to probe-in-air except that a fluid of known viscosity, 80 centipoise at 37 degrees C., is added to disposable cuevette A38. Cuevette A38 must be filled completely so the fluid is level across the top of cuevette A38. Also, the filled cuevette must remain on cuevette holder A40 with head assembly A24 closed for sufficient time to reach temperature equilibrium. Typically, 15 minutes are necessary to ensure temperature stability of the fluid within cuevette A38. This configuration is referred to as probe-in-reference.

Signal conditioning circuit A58 is calibrated for offset while in the probe-in-air configuration. Variable resistor RV3 is adjusted to achieve 0.0 mV for analog output voltage signal V62. Next, a probe-in-reference configuration is set up, and variable resistor RV2 is adjusted to select 5.3 mV for analog output voltage signal V62. This entire process is repeated until calibration is stable at both calibration points. Typically, the calibration remains stable after two calibration cycles.

Calibration of microcontroller U44 is initiated by invoking a calibration routine that is one of the normal routines to be executed by microcontroller U44. This routine can only be executed if calibration mode select jumper A68 is installed. The calibration routine is initiated by moving the MIX/ZERO switch A22 to the ZERO position. The routine prompts the operator to first set up the probe-in-air configuration and then the probe-in-reference configuration. Calibration coefficients for offset and gain are stored in EEPROM U70, as set forth above, in units of 0.2 hertz. The calibration coefficient for offset is the measured value of analog output voltage signal V62 while the instrument is in the probe-in-air configuration. The calibration coefficient for gain is the difference of the measured values of analog output voltage signal V62 when the instrument is in the probe-in-reference configuration and when the instrument in the probe-in-air configuration.

During operation of the instrument (calibration mode select jumper A68 not installed) oscillator gain voltage signal V56 will drift due to variations in ambient humidity. This drift corrupts both the offset of analog output voltage signal V62 and the offset calibration of microcontroller U44. The offset of analog output voltage signal V62 can be corrected by adjusting the zero offset on the external strip chart recorder. The offset calibration of microcontroller U44 can be reset by moving the MIX/ZERO switch A22 to the ZERO position while the instrument is in the probe-in-air configuration.

Figure 9A:
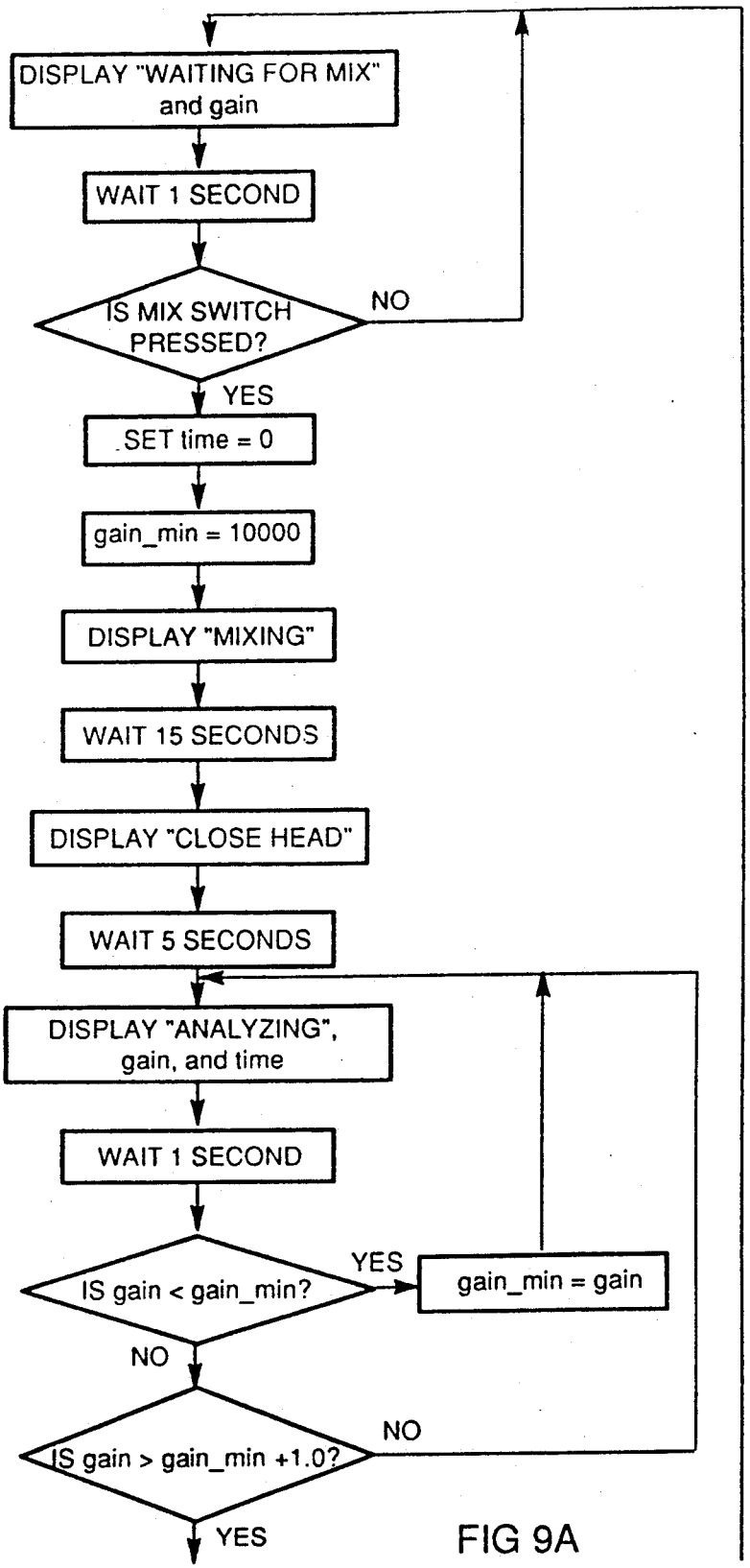
FIGS. 9A-B are a flow chart illustrating overall operation of the automated analysis process performed by the viscoelastic test instrument of the present invention.
Figure 9B:
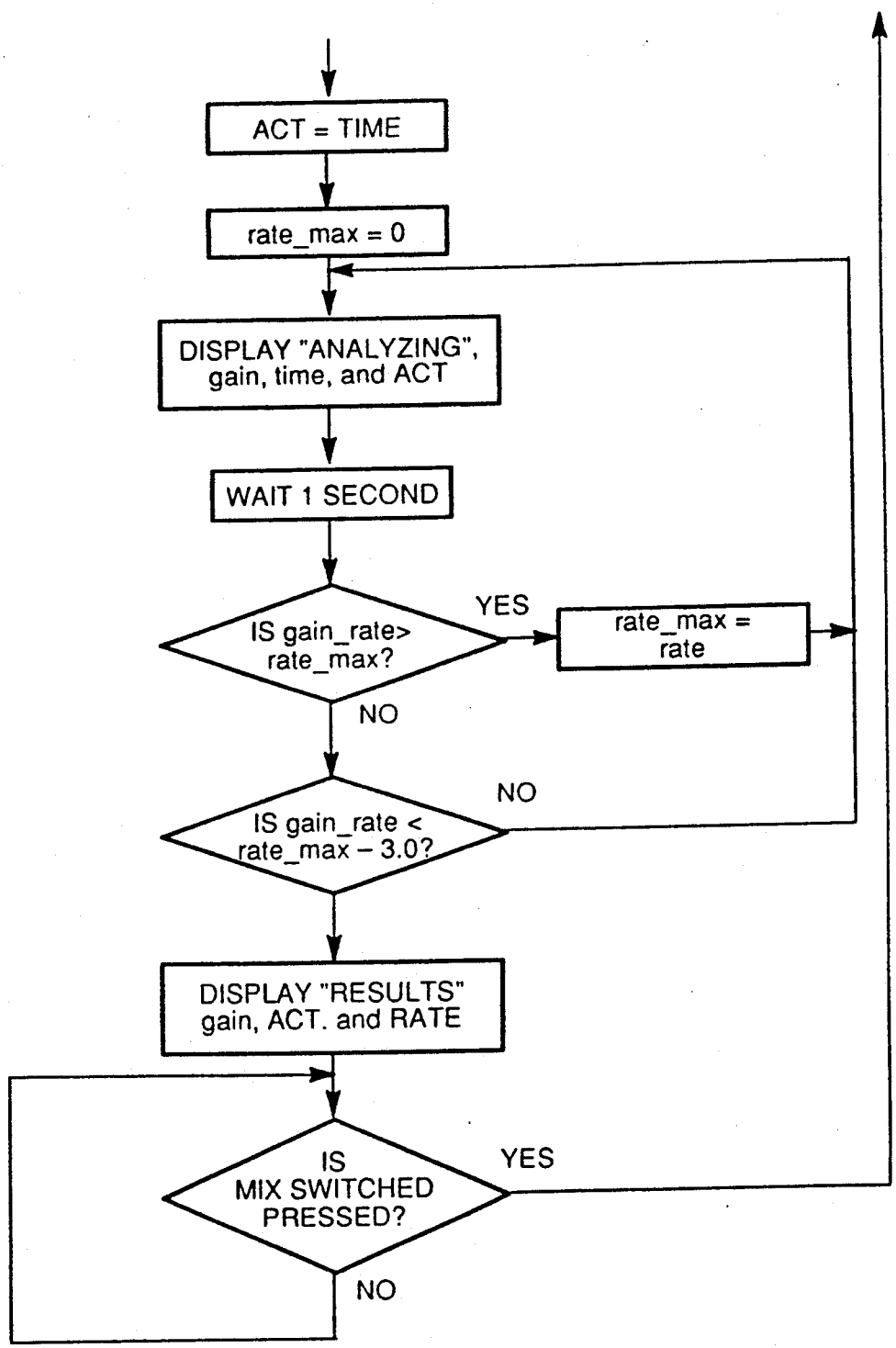
Figure 10A:
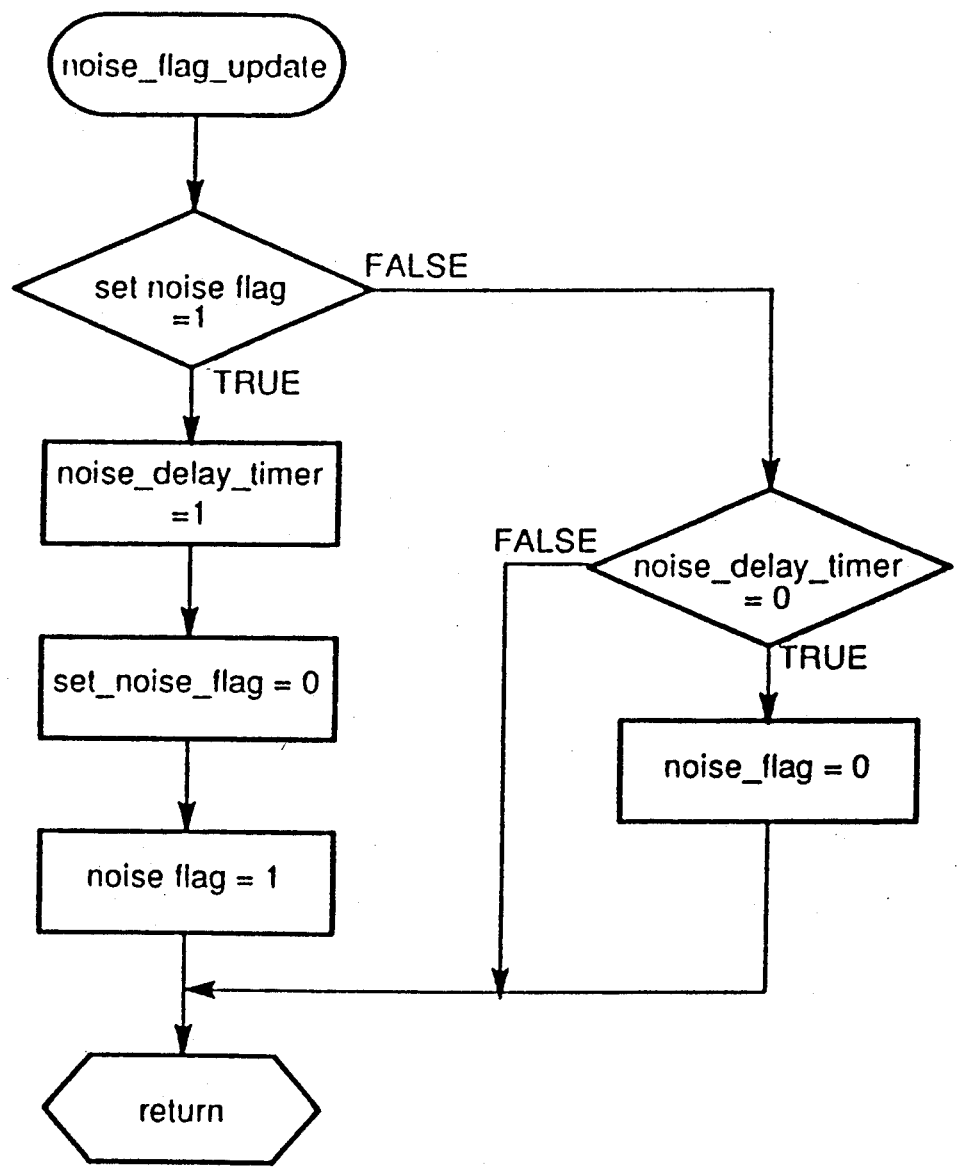
FIGS. 10A-E are flow charts of routines used to perform the software controlled analog to digital measurement and digital noise filtering of oscillator gain frequency in the fluid viscoelastic test instrument of the present invention.
Figure 10B:
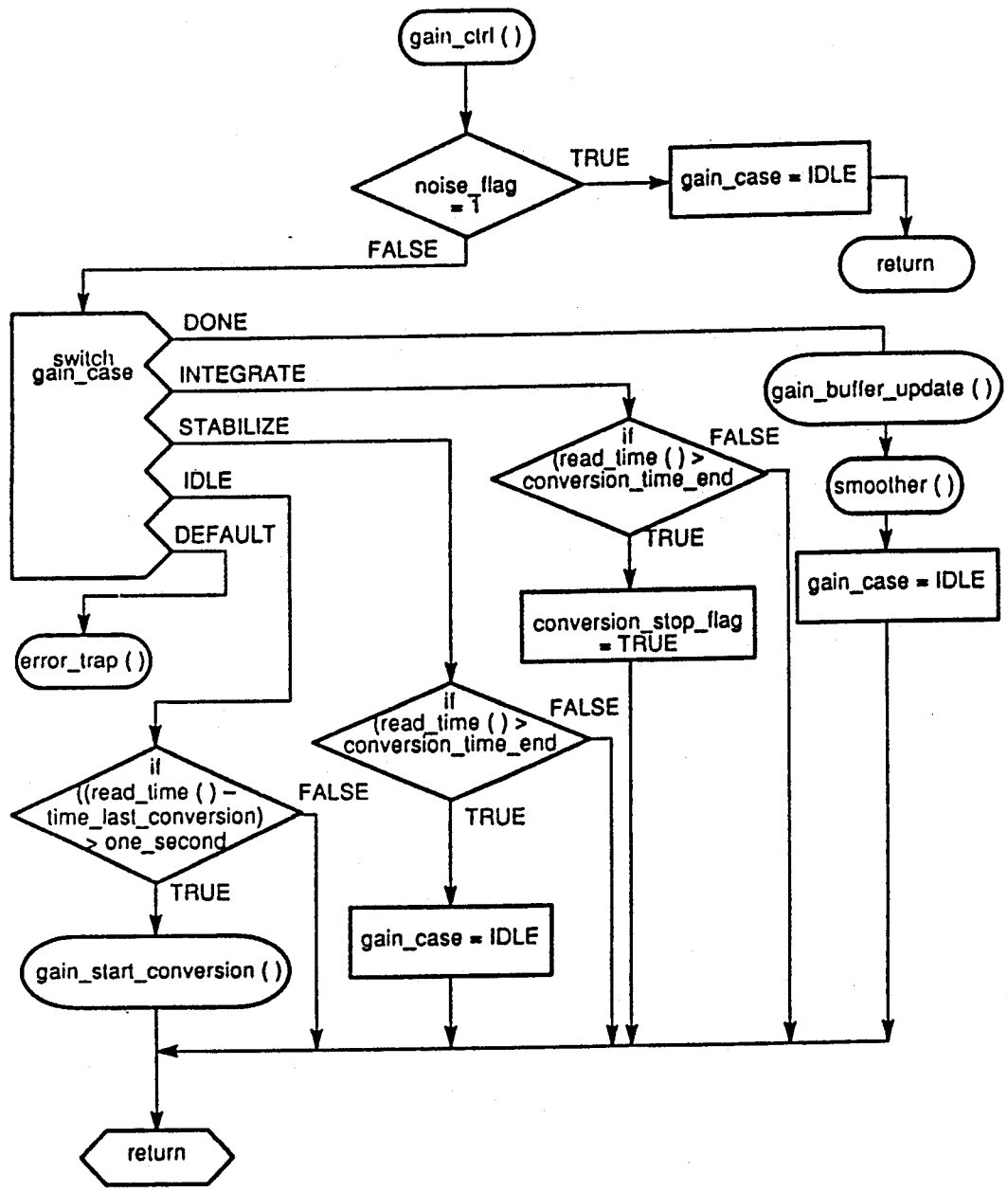
Figure 10C:
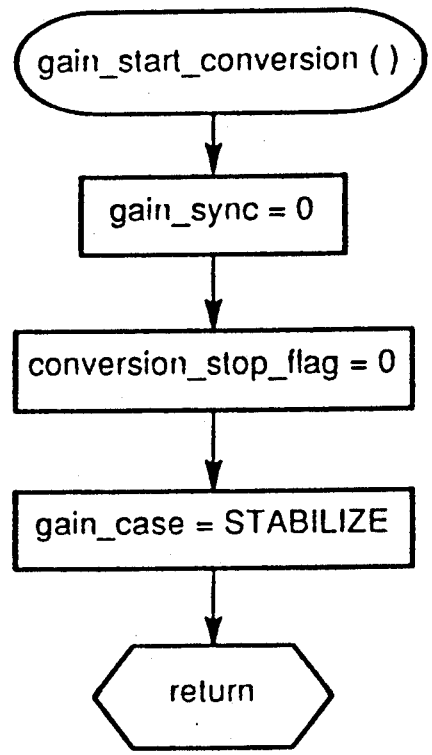
Figure 10D:
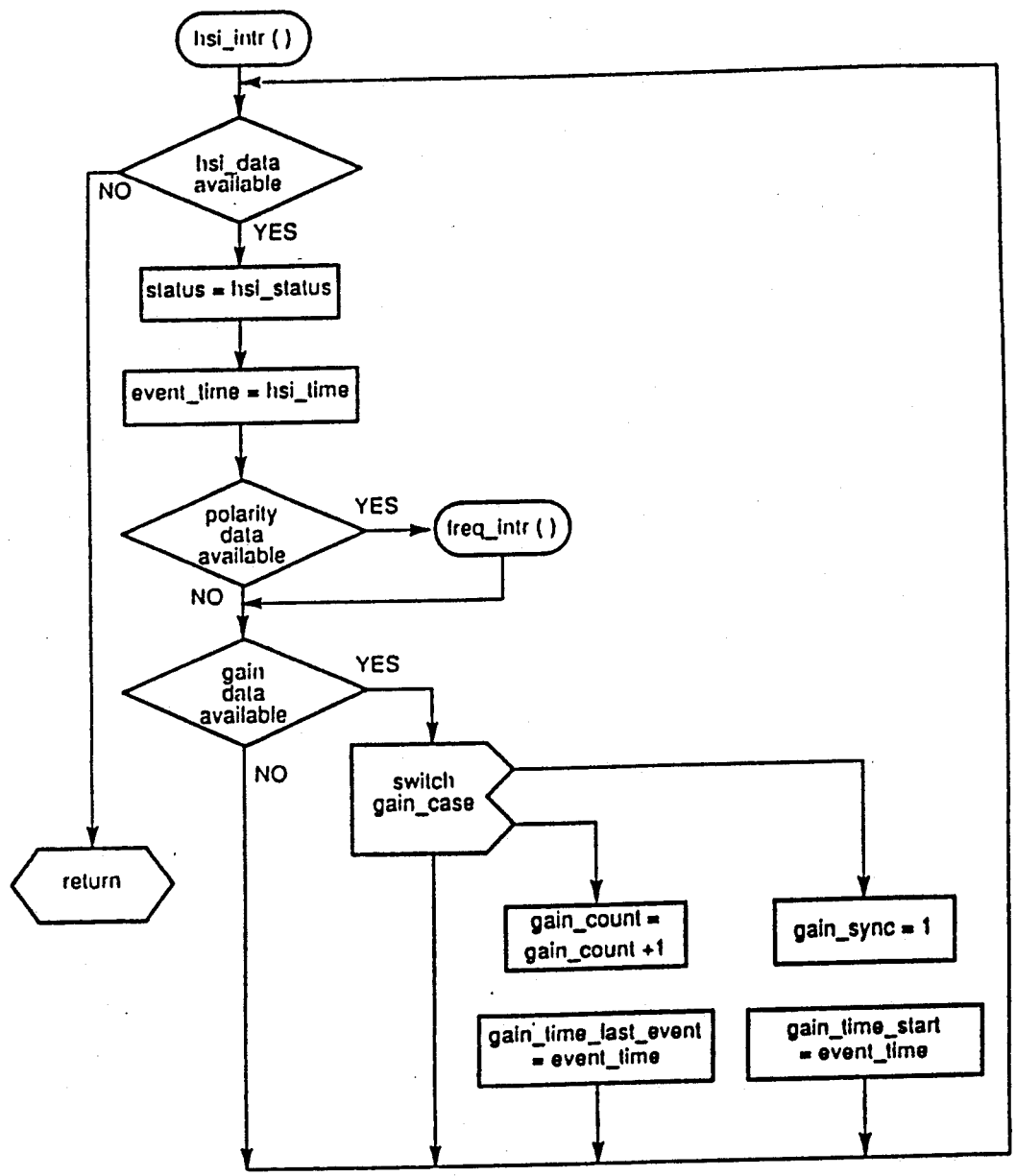
Figure 10E:
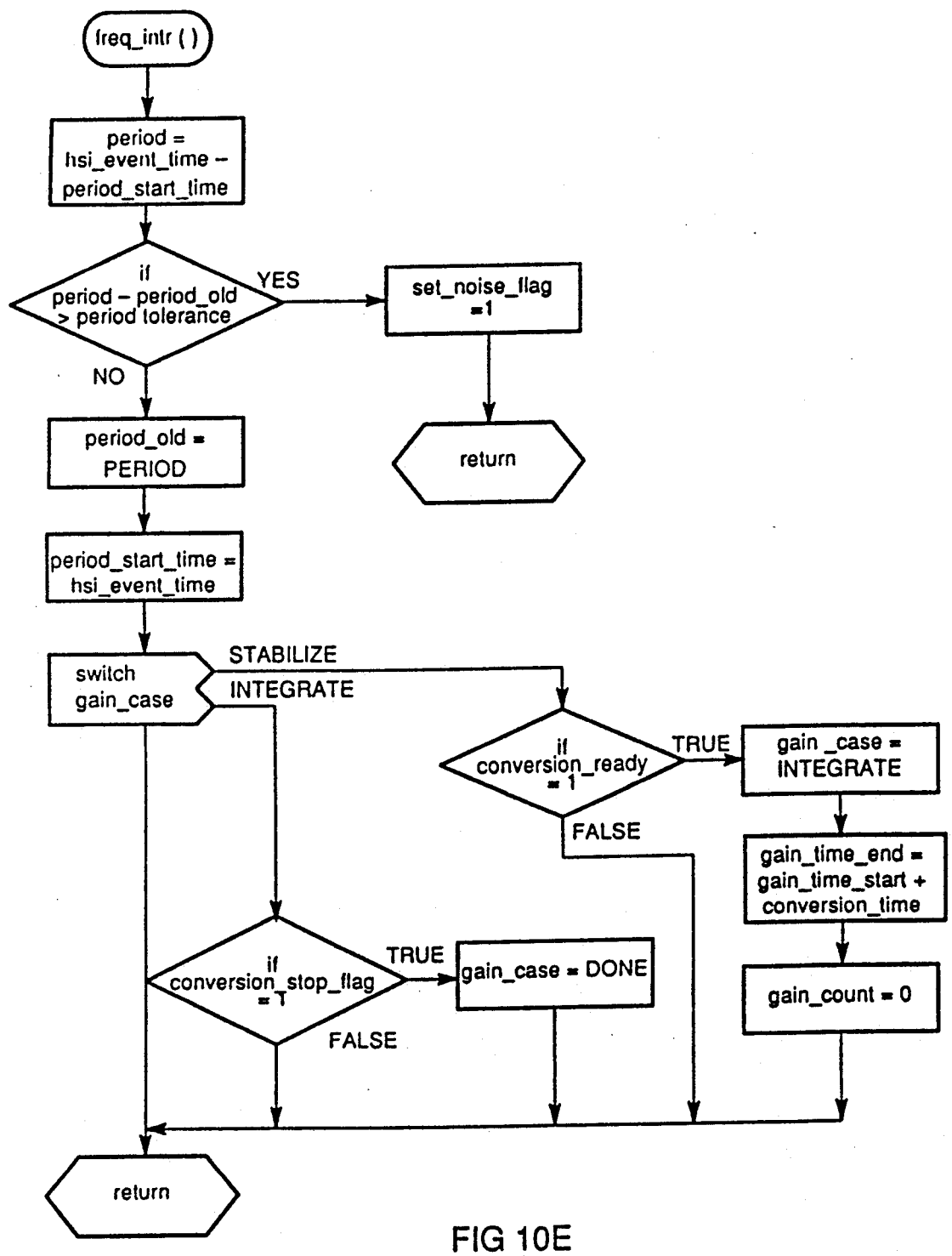

Following calibration of the viscoelastic test instrument of the present invention as described above, operation of the instrument to analyze a blood sample involves a precise sequence of steps. As an aid to the user, display A32 displays both user prompts and analysis results. The flowchart of FIGS. 9A and 9B relates the operation of the viscoelastic test instrument throughout an analysis cycle. Prior to initiating analysis of a blood sample, the instrument displays the message "WAITING FOR MIX" on the top line of display A32 and the current value for SIGNAL (the calibrated representation of oscillator gain voltage signal V56) on the bottom line of display A32. The instrument is configured in the probe-in-air arrangement. The zero control of an external stripchart recorder is adjusted to position the stripchart recorder pen to the zero position on the stripchart paper. The MIX/ZERO switch A22 is momentarily raised to the ZERO position to zero the measured value for oscillator gain voltage signal V56, thereby setting the value displayed for SIGNAL to be near 0.0. The stripchart recorder paper speed is adjusted to 0.5 cm. per minute.

Next, the head assembly A23 is raised, a cuevette containing a 0.4 ml. blood sample and stirring bar is placed in cuevette holder A40. A contact activator is added to the sample, and MIX/ZERO switch A22 is momentarily pressed to the MIX position. The viscoelastic test instrument responds to actuation of the MIX/ZERO switch A22 by engaging the mixing motor A42, by displaying the message "MIXING" on the top line of display A32, and by initiating the automated analysis of the blood sample. After 10 seconds of analysis, mixing motor A42 stops. After 15 seconds of analysis, the message "CLOSE HEAD" is displayed on the top line of display A32. At this time the user closes head assembly A23. After 20 seconds of analysis, the message "ANALYZING" is displayed on the top line of the display A32, and the current measured value of oscillator gain voltage signal V56 is displayed on the second line of display A32 above the SIGNAL legend. The elapsed time of analysis is displayed on the second line of display A32 above the TIME egend. The message "???" is displayed on the second line of display A32 above both the ACT and RATE legends. After 35 seconds of analysis, the software executed by microcontroller U44 begins to check the measured value of oscillator gain voltage signal V56 for viscoelastic changes in the blood sample. During this analysis period, the minimum value for the measured value of oscillator gain voltage signal V56 is saved. The current value of the measured value of oscillator gain voltage signal V56 is compared against this minimum saved value. When 1% of full scale variation in the measured value of oscillator gain voltage signal V56 is detected, the activated clotting time period (ACT) A76 is set to the current value of analysis time. After detection of the activated clotting time period (ACT) A76, the message "ANALYZING" remains on the top line of display A32; the current measured value of oscillator gain voltage signal V56 is displayed on the top line of display A32 above the SIGNAL legend; the elapsed analysis time is displayed on the second line of display A32 above the TIME legend; the calculated value of activated clotting time (ACT) A76 is displayed on the second line of display A32 above the ACT legend; and the message "???" is displayed above the RATE legend on the second line of display A32.

The analysis of a blood sample continues to determine a value for rate of clot formation (RATE) A80. This analysis stores a maximum value for the rate of change in measured oscillator gain voltage signal V56 versus time. The current rate of change of measured oscillator gain voltage signal V56 is compared with the stored maximum value of this parameter. When the current value of the rate of change of measured oscillator gain voltage V56 is less than the maximum stored value of this parameter minus 3.0% per minute, this maximum value is determined to be the rate of clot formation (RATE) A80. At this point, the message "RESULTS" is displayed on the top line of display A32. The current measured value of oscillator gain voltage signal V56, activated clotting time (ACT) A76, and rate of clot formation (RATE) are displayed on the second line of display A32 above the SIGNAL, ACT, and RATE legends, respectively. This display continues until a new analysis cycle is commenced on another blood sample by inserting a new cuevette and moving the MIX/ZERO switch A22 to the MIX position.

```
/* Source code for GAIN.C
** This module contains the task, sono_analyze(), and support routines.
*/ define TRUE 1
define FALSE 0
#define ON 1
#define OFF 0
#define SONO_INIT 0
#define SONO_FACTORY_CAL 1
#define SONO_ANALYZE 2
#define SONO_IDLE 3
#define IDLE_DELAY 8
#define SUBCASE_0 0
#define SUBCASE_1 1
#define SUBCASE_2 2
#define SUBCASE_3 3
#define SUBCASE_4 4
#define SUBCASE_5 5
#define SUBCASE_6 6
#define SUBCASE_7 7
#define SUBCASE_8 8
#define SONO_BUFFER_LENGTH 10
#define FOUR_MINUTES 4800
#define ONE_SECOND 20
```

```
#define TEN_SECONDS 200
#define TWO_SECONDS 40
#define FIFTEEN_SECONDS 300
#define SONO_MINIMUM_DELAY 700
define SONORATE_THRESHOLD 60 struct gain_data
   {
   unsigned data;
   unsigned time;
   };

struct device_state
   {
   unsigned char state, substate;
   };

extern struct gain_data gain_table[SONO_BUFFER_LENGTH];
/* gain_table[]          stores the most recent time dated measurements of
**                       oscillator gain frequency
*/ extern struct device_state sono;
/* sono                  stores the current state and substate of operation
*/ extern int gain;
/* gain                  stores the most recent filtered value for
**                       oscillator gain frequency

*/ extern int gain_minimum;
/* gain_minimum          stores the minimum value of gain.  Used to
**                       calculate ACT.
*/ extern unsigned ACT, ACT_found;
/* ACT                   the value of ACT calculated for the current
**                       sample.
** ACT_found             a flag that is TRUE when ACT has been
**                       successfully found for a sample.
*/ extern int RATE;
/* RATE                  the RATE of the current sample.  The first
**                       maximum of the slope of gain after ACT has been
**                       found.
*/ extern int gain_rate;
/* gain_rate             the slope of gain.
*/ extern unsigned sono_time, second_20;
/* sono_time             a general purpose variable. Normally used
**                       for timing purposes.
** second_20             the time that an analysis has progressed.
**                       Units are in 1/20 seconds.
*/
```

```c
extern char display_second;
/* display_second        a flag to enable displaying seconds on the
**                       LCD display
*/ extern char noise_flag;
/* noise_flag            noise_flag is TRUE when noise has been detected
**                       on oscillator polarity input signal.
*/ void puts40(char *);
void beeper(int);
void time_reset(void);
void hsi_reset(void);
nonreentrant void sono_analyze(void);
unsigned average_x(void);
unsigned sonoACT_calc(void);

void mix_abort_check()
/* abstract: abort task in progress if mix_button is pressed. */
   {
   if (mix_button())
      {
      sono.substate = SUBCASE_0;
      sono.state = SONO_ANALYZE;
      RATE = ACT = 0;
      }
   } void zero_abort_check()
/* abstract: abort task in progress if zero_button is pressed. */
   {
   if (zero_button())
      {
      sono_idle_setup();
      }
   } nonreentrant void sono_analyze()
/* abstract: coordinates activities related to analyzing a sample for ACT
**           and RATE. */
   {
   char i;
   switch (sono.substate)
      {
      case SUBCASE_0:
         time_reset();
         hsi_reset();
         sono.substate = SUBCASE_1;
         sono_time = second_20+TEN_SECONDS;
         lcd_clear();
         puts40("Mixing...");
         RATE = ACT = 0;
         break;
      case SUBCASE_1:
         zero_abort_check();
         if (second_20 > sono_time)
            {
```

```c
            display_second = TRUE;
            ACT = RATE = 0;
            sono.substate = SUBCASE_2;
            puts40("Close Head");
            for (i=0; i<SONO_BUFFER_LENGTH; i++)
               {
               gain_table[i].data = 0;
               }
            }
         break;
      case SUBCASE_2:
         zero_abort_check();
         if (second_20 > FIFTEEN_SECONDS)
            {
            sono.substate = SUBCASE_3;
            gain_minimum = 20000;
            puts40("Analysing...");
            }
         break;
      case SUBCASE_3:
         mix_abort_check();
         zero_abort_check();
         if (second_20 % 20 == 0)
            {
            if (noise_flag)
               {
               puts40("Analysing: NOISE");
               }
            else
               {
               puts40("Analysing...");
               }
            }
         display_results();
         if ((second_20 > SONO_MINIMUM_DELAY) && (gain_minimum > gain) &&
            (gain_table[SONO_BUFFER_LENGTH-1].data > 0))
            {
            gain_minimum = gain;
            }
         if ((ACT = ACT_calc()) > 0)
            {
            ACT = (second_20 + 10) /20;
            beeper(ON);
            gain_minimum = -100;
            sono.substate = SUBCASE_4;
            sono_time = second_20+ONE_SECOND;
            ACT_found = TRUE;
            }
         if ((second_20/20) > 998)
            {
            lcd_clear();
            beeper(ON);
            sono.substate = SUBCASE_6;
            sono_time = second_20 + TWO_SECONDS;
            puts("SonACT not found");
            }
         break;
      case SUBCASE_4:
```

```
          {
          beeper(OFF);
          sono.substate = SUBCASE_5;
          sono_time = second_20+FOUR_MINUTES;
          }
       break;
case SUBCASE_5:
       mix_abort_check();
       zero_abort_check();
       if (second_20 % 20 == 0)
          {
          if (noise_flag)
             {
             puts40("Analysing: NOISE");
             }
          else
             {
             puts40("Analysing...");
             }
          }
       display_results();
       if (gain_minimum < gain_rate)
          {
          gain_minimum = gain_rate;
          }
       if ((sono_time < second_20) ||
           (gain_minimum > gain_rate + SONORATE_THRESHOLD))
          {
          RATE = gain_minimum;
          lcd_clear();
          beeper(ON);
          sono.substate = SUBCASE_6;
          sono_time = second_20 + TWO_SECONDS;
          puts("Results");
          }
       break;
case SUBCASE_6:
       mix_abort_check();
       zero_abort_check();
       display_second = FALSE;
       if (sono_time < second_20)
          {
          time_reset();
          hsi_reset();
          beeper(OFF);
          sono.substate = SUBCASE_7;
          }
       break;
case SUBCASE_7:
       mix_abort_check();
       zero_abort_check();
       display_results();
       if (second_20 > 998)
          {
          time_reset();
          hsi_reset();
          }
       break;
default:
       error_trap("ERR: ANALYZE");
```

```c
/* Source code for ad.c
** This module contains routines used in measuring oscillator gain frequency
** and calculating global variables gain and gain_rate.
*/ define TRUE 1
define FALSE 0
#define SONO_BUFFER_LENGTH 10
#define IDLE 0
#define STABILIZE 1
#define INTEGRATE 2
#define DONE 3
#define CONVERSION_TIME 650000
#define NOISE_DELAY 40
define TICKS_ONE_SECOND 500000 struct long_parts
    {
    unsigned int least;
    unsigned int most;
    };

union long_and_parts
    {
    unsigned long whole;
    struct long_parts parts;
    };

struct gain_data
    {
    unsigned data;
    unsigned time;
    };

unsigned long read_time(void);
void gain_update_buffer(void);
void freq_intr(void);

/* 80c196 special function registers */
extern volatile unsigned short hsi_time;    /*r*/
extern volatile unsigned char hsi_status;   /*r*/
extern volatile unsigned char ios1;         /*r*/ extern unsigned long period_start;
/* period_start         the time when a measurement of oscillator
**                      period begins
*/ extern unsigned period_old, period;
/* period               the most recent measurement of oscillator
**                      period. Units are 2 microseconds per count.
** period_old           The previous value of period.
*/ extern union long_and_parts event_time;
/* event_time           the time corresponding to the most recent
**                      hsi interrupt.
*/
```

```
extern unsigned hsi_old_time;
/* hsi_old_time         the time (16 bits) for the previous reading
**                      of event_time.
*/ extern unsigned char status;
/* status               stores a value of hsi_status for analysis
*/ extern struct gain_data gain_table[SONO_BUFFER_LENGTH];
/* gain_table[]         stores the most recent time dated measurements of
**                      oscillator gain frequency
*/ extern unsigned char noise_flag_set;
/* noise_flag_set       a flag set during an interrupt to enable the
**                      noise filter.
*/ extern unsigned char noise_flag;
/* noise_flag           noise_flag is TRUE when noise has been detected
**                      on oscillator polarity input signal.
*/ extern unsigned char conversion_stop_flag;
/* conversion_stop_flag a flag to stop an integration of gain.
*/ extern unsigned char gain_case;
/* gain_case            the case of the current measurement of gain
*/ extern unsigned char gain_sync;
/* gain_sync            a flag used in syncronizing the integration of
**                      gain to a transition of oscillator polarity.
*/ extern unsigned long gain_time_start, gain_time_end, gain_time_last_event;
/* gain_time_start,
** gain_time_end,
** gain_time_last_event general variables used in integration of gain
**                      frequency input.
*/ extern unsigned long time_last_conversion;
/* gain_time_last conversion stores time of most recent measurement of gain
*/ extern unsigned gain_count;
/* gain_count           variable used in integration of gain frequency
**                      input.
*/ extern unsigned noise_delay_timer;
/* noise_delay_timer    used as a delay timer to temperarily keep noise
**                      filter active after a noise event.
*/
```

```
extern int gain;
/* gain                   stores the most recent filtered value for
**                        oscillator gain frequency
*/ extern int gain_rate;
/* gain_rate              the slope of gain.
*/ extern unsigned gain_cal[2];
/* gain_cal[0]            offset calibration constant for gain measurement.
**                        corresponds to frequency at probe-in-air setup.
** gain_cal[1]            gain calibration constant for gain measurement.
**                        corresponds to difference in frequencies between
**                        probe-in-reference and probe-in-air calibration
**                        points.
*/ nonreentrant void hsi_intr()
/* abstract: interrupt routine.  Entered when data is available on HSI. */
   {
   while (iosl & 0x80)
      {
      status = hsi_status;
      event_time.parts.least = hsi_time;
      if (hsi_old_time > event_time.parts.least)
         event_time.parts.most++;
      hsi_old_time = event_time.parts.least;
      if (status & 0x4)
         {
         freq_intr();
         }
      if (status & 0x01)
         {
         switch (gain_case)
            {
            case STABILIZE:
               gain_sync = TRUE;
               gain_time_start = event_time.whole;
               break;
            case INTEGRATE:
               gain_count++;
               gain_time_last_event = event_time.whole;
               break;
void freq_intr()
   {
   if (event_time.whole < period_start)
      error_trap("ERR: gain_ctrl()");
   period = event_time.whole - period_start;
   if (period_old > (period + 32))
      {
      noise_flag_set = TRUE;
      }
   if (period > (period_old + 32))
      {
      noise_flag_set = TRUE;
      }
   period_old = period;
```

```
    period_start = event_time.whole;
    switch (gain_case)
        {
        case STABILIZE:
            if (gain_sync)
                {
                gain_case = INTEGRATE;
                gain_time_end = gain_time_start
                        + CONVERSION_TIME;
                gain_count = 0;
                }
            break;
        case INTEGRATE:
            if (conversion_stop_flag)
                {
                gain_case = DONE;
                }
            break;
        }
    } nonreentrant void gain_start_conversion()
/* abstract: performs assignments required to start a measurement of gain. */
    {
    gain_sync = FALSE;
    conversion_stop_flag = FALSE;
    gain_case = STABILIZE;
    } nonreentrant void gain_ctrl()
/* abstract: tast to coordinate measurements of gain input frequency */
    {
    if (noise_flag)
        {
        gain_case = IDLE;
        return;
        }
    switch (gain_case)
        {
    case IDLE:
        if ((read_time() - time_last_conversion) > TICKS_ONE_SECOND)
            {
            gain_start_conversion();
            }
        break;
    case STABILIZE:
        if (read_time() > gain_time_end)
            {
            gain_case = IDLE;
            }
        break;
    case INTEGRATE:
        if (read_time() > gain_time_end)
            {
            conversion_stop_flag = TRUE;
            }
        break;
    case DONE:
```

```
            gain_update_buffer();
            smoother();
            gain_case = IDLE;
            break;
        default:
            error_trap("ERR: gain_ctrl");
        }
    } nonreentrant void gain_update_buffer()
/* abstract: updates gain_table[] with latest measurement of gain frequency */
    {
    long x0;
    unsigned char i;
    for (i = SONO_BUFFER_LENGTH-1; i > 0; i--)
        {
        gain_table[i].data = gain_table[i-1].data;
        gain_table[i].time = gain_table[i-1].time;
        }
    x0 = (gain_time_last_event - gain_time_start)/10;
    gain_table[0].data = (2500001 * (long)gain_count) / x0;
    gain_table[0].time = (gain_time_last_event +
                gain_time_start) / 15001;
    } nonreentrant smoother()
/* abstract: a smoothing filter to remove glitches in gain measurements. */
/*           updates global variables gain and gain_rate. */
    {
    long xx;
    int x[4];
    unsigned char i;

for (i=0; i<4; i++)
        {
        xx = (long)(((long)((long)gain_table[i].data -
             (long)gain_table[i+1].data)) * 10001) /
             ((long)gain_table[i].time - (long)gain_table[i+1].time);
        x[i] = xx;
        }
    for (i=0; i<3; i++)
        {
        x[i] = x[i] - x[i+1];
        }
    if (((x[0] > 0) && (x[1] < 0) && (x[2] > 0)) ||
        ((x[0] < 0) && (x[1] > 0) && (x[2] < 0)))
        {
        xx = gain_table[1].data;
        xx = (xx + gain_table[3].data) / 2;
        gain_table[2].data = xx;
        xx = gain_table[1].time;
        if (gain_table[1].time < gain_table[3].time)
            xx += 0x10000;
        xx = (xx + gain_table[3].time) / 2;
        gain_table[2].time = xx;
        }
    xx = 5401 * ((long)average_x() - (long)gain_cal[0]) /
             ((long)gain_cal[1]);
    gain = xx;
```

```
{
xx = (gain_table[SONO_BUFFER_LENGTH-1-i].time
        < gain_table[SONO_BUFFER_LENGTH-6-i].time) ?
    (long)gain_table[SONO_BUFFER_LENGTH-6-i].time
        - (long)gain_table[SONO_BUFFER_LENGTH-1-i].time:
    (long)gain_table[SONO_BUFFER_LENGTH-6-i].time + 0x100001
        - (long)gain_table[SONO_BUFFER_LENGTH-1-i].time;
xx = (((long)gain_table[SONO_BUFFER_LENGTH-6-i].data -
      (long)gain_table[SONO_BUFFER_LENGTH-1-i].data)
      * 600001) / xx;
xx = (xx * 5401) / ((long)gain_cal[1]);
x[i] = xx;
}
for (i=0, xx=0; i<3; i++)
{
xx += (long)x[i];
}
xx /= 3;
gain_rate = xx;
} void noise_flag_update()
/* abstract: task to update noise filter */
/* note: noise_delay_timer is decremented (externally) every 1/20 seconds */
{
if (noise_flag_set)
{ noise_flag_set = FALSE;
noise_delay_timer = NOISE_DELAY;
noise_flag = TRUE;
return;
}
if (noise_delay_timer == 0)
{
noise_flag = FALSE;
}
}
```

I claim:

1. An instrument for measuring one or more viscoelastic properties of a fluid sample, the instrument comprising:

probe means disposed in contact with the fluid sample;

electromechanical transducer means coupled to the probe means for providing mechanical displacement of the probe means relative to the fluid sample;

first circuit means, connected to the electromechanical transducer means, said first circuit means comprising drive circuitry providing a drive signal for generating oscillatory mechanical displacement of the probe means relative to the fluid sample, said first circuit means further comprising response circuitry for monitoring a response signal generated by the electromechanical transducer means, the response signal being representative of the one or more viscoelastic properties of the fluid sample, said drive circuitry and response circuitry forming a feedback loop wherein the drive signal is developed from the response signal and vice versa;

second circuit means for regulating an amplitude of a first signal within said feedback loop, while allowing said feedback loop to operate at resonant oscillatory frequency determined by said probe means, said electromechanical transducer means, and said first circuit means; and microcontroller means for receiving and analyzing said response signal to determine the one or more viscoelastic properties of the fluid sample represented by said response signal, said microcontroller means being responsive to said response signal for computing a time period thereof between a measurement start time and the occurrence of a viscoelastic change in the fluid sample represented by said response signal.

2. An instrument for measuring one or more viscoelastic properties of a fluid sample as in claim 1 wherein the occurrence of a viscoelastic change in said fluid sample is represented by a point in time at which a signature amplitude of said response signal varies by one percent of a full scale amplitude from an initial steady state signature amplitude thereof, and wherein said time period represents an activated clotting time of said fluid sample.

3. An instrument for measuring one or more viscoelastic properties of a fluid sample as in claim 2 further comprising display means coupled to said microcontroller means, said display means being operative for visually displaying said activated clotting time to the user.

4. An instrument for measuring one or more viscoelastic properties of a fluid sample as in claim 1 wherein said microcontroller means is responsive to said response signal for computing a quantified intensity of said viscoelastic change in the fluid sample.

5. An instrument for measuring one or more viscoelastic properties of a fluid sample as in claim 4 wherein said microcontroller means is responsive to said response signal for computing a first maximum slope of a signature of said response signal following the occurrence of said viscoelastic change in the fluid sample, said first maximum slope representing a rate of clot formation of said fluid sample.

6. An instrument for measuring one or more viscoelastic properties of a fluid sample as in claim 5 further comprising display means coupled to said microcontroller means, said display means being operative for visually displaying said rate of clot formation computed by said microcontroller means.

7. An instrument for measuring one or more viscoelastic properties of a fluid sample as in claim 1 further comprising integrating A-D converter means coupled to said first and second circuit means for providing increased resolution of the amplitude of said response signal.

8. An instrument for measuring one or more viscoelastic properties of a fluid sample as in claim 7 further comprising means for synchronizing an integration period of said integrating A-D converter means with a period of said drive signal for providing a correction for AC ripple that may be present on said drive signal.

9. An instrument for measuring one or more viscoelastic properties of a fluid sample as in claim 8 further comprising polarity detector means coupled to said first and second circuit means for determining a polarity of said response signal and for synchronizing said integration period of said integrating A-D converter with determinations of polarity made by said polarity detector means.

10. An instrument for measuring one or more viscoelastic properties of a fluid sample as in claim 9 wherein said microcontroller means is operative, in response to determinations of polarity of said response signal made by said polarity detector means, for detecting unexpected variances in a frequency of said response signal produced by extraneous noise sources and for disabling said integrating A-D converter means for a predetermined period of time following detection of said unexpected variances in the frequency of said response signal.

11. An instrument for measuring one or more viscoelastic properties of a fluid sample as in claim 10 further comprising display means coupled to said microcontroller means for visually displaying messages to the user; and wherein said microcontroller means is operative, following detection of unexpected variances in the frequency of said response signal, for generating a message on said display means indicating the presence of noise to the user.

12. An instrument for measuring a plurality of viscoelastic properties of a fluid sample, the instrument comprising:

probe means disposed in contact with the fluid sample;

electromechanical transducer means coupled to the probe means for providing mechanical displacement of the probe means relative to the fluid sample;

first circuit means, connected to the electromechanical transducer means, said first circuit means comprising drive circuitry providing a drive signal for generating oscillatory mechanical displacement of the probe means relative to the fluid sample, said first circuit means further comprising response circuitry for monitoring a response signal generated by the electromechanical transducer means, the response signal being representative of the plurality of viscoelastic properties of the fluid sample, said drive circuitry and response circuitry forming a feedback loop wherein the drive signal is developed from the response signal and vice versa;

second circuit means for regulating an amplitude of a first signal within said feedback loop; and microcontroller means for receiving and analyzing said response signal to determine said plurality of viscoelastic properties of the fluid sample represented by said response signal, said microcontroller means being responsive to said response signal for computing a time period thereof between a measurement start time and the occurrence of a viscoelastic change in the fluid sample represented by said response signal.

13. An instrument for measuring one or more viscoelastic properties of a fluid sample as in claim 12 wherein the occurrence of a viscoelastic change in said fluid sample is represented by a point in time at which a signature amplitude of said response signal varies by one percent of a full scale amplitude form an initial steady state signature amplitude thereof, and wherein said time period represents an activated clotting time of said fluid sample.

14. An instrument for measuring one or more viscoelastic properties of a fluid sample as in claim 13 further comprising display means coupled to said microcontroller means, said display means being operative for visually displaying said activated clotting time to the user.

15. An instrument for measuring one or more viscoelastic properties of a fluid sample as in claim 12 wherein said microcontroller means is responsive to said response signal fro computing a quantified intensity of said viscoelastic change in the fluid sample.

16. An instrument for measuring one or more viscoelastic properties of a fluid sample as in claim 15 wherein said microcontroller means is responsive to said response signal for computing a first maximum slope of a signature of said response signal following the occurrence of said viscoelastic change in the fluid sample, said first maximum slope representing a rate of clot formation of said fluid sample.

17. An instrument for measuring one or more viscoelastic properties of a fluid sample as in claim 16 further comprising display means coupled to said microcontroller means, said display means being operative for visually displaying said rate of clot formation computed by said microcontroller means.

18. An instrument for measuring one or more viscoelastic properties of a fluid sample as in claim 12 further comprising integrating A-D converter means coupled to said first and second circuit means for providing increased resolution of the amplitude of said response signal.

19. An instrument for measuring one or more viscoelastic properties of a fluid sample as in claim 18 further comprising means for synchronizing an integration period of said integrating A-D converter means with a period of said drive signal for providing a correction for AC ripple that may be present on said drive signal.

20. An instrument for measuring one or more viscoelastic properties of a fluid sample as in claim 19 further comprising polarity detector means coupled to said first and second circuit means for determining a polarity of said response signal and for synchronizing said integration period of said integrating A-D converter with determinations of polarity made by said polarity detector means.

21. An instrument for measuring one or more viscoelastic properties of a fluid sample as in claim 20 wherein said microcontroller means is operative, in response to determinations of polarity of said response signal made by said polarity detector means, for detecting unexpected variances in a frequency of said response signal produced by extraneous noise sources and for disabling said integrating A-D converter means for a predetermined period of time following detection of said unexpected variances in the frequency of said response signal.

22. An instrument for measuring one or more viscoelastic properties of a fluid sample as in claim 21 further comprising display means coupled to said microcontroller means for visually displaying messages to the user; and wherein said microcontroller means is operative, following detection of unexpected variances in the frequency of said response signal, for generating a message on said display means indicating the presence of noise to the user.

* * * * *